United States Patent
Ohgiya et al.

(10) Patent No.: US 7,750,019 B2
(45) Date of Patent: Jul. 6, 2010

(54) PYRIMIDINE COMPOUND HAVING BENZYL(PYRIDYLMETHYL)AMINE STRUCTURE AND MEDICAMENT COMPRISING THE SAME

(75) Inventors: Tadaaki Ohgiya, Saitama (JP); Toru Miura, Tokyo (JP); Ayumu Okuda, Tokyo (JP); Toshiharu Arai, Saitama (JP); Koichi Yamazaki, Tokyo (JP); Taro Aoki, Saitama (JP); Katsutoshi Miyosawa, Saitama (JP); Haruki Shibata, Tokyo (JP); Kimiyuki Shibuya, Saitama (JP)

(73) Assignee: Kowa Company, Ltd., Aichi (JP)

( * ) Notice: Subject to any disclaimer, the term of this patent is extended or adjusted under 35 U.S.C. 154(b) by 120 days.

(21) Appl. No.: 11/835,127

(22) Filed: Aug. 7, 2007

(65) Prior Publication Data
US 2009/0054474 A1 Feb. 26, 2009

Related U.S. Application Data

(60) Provisional application No. 60/836,948, filed on Aug. 11, 2006.

(51) Int. Cl.
*C07D 239/42* (2006.01)
*A61K 31/505* (2006.01)
(52) U.S. Cl. .................. 514/275; 544/331
(58) Field of Classification Search .............. 544/331; 514/275
See application file for complete search history.

(56) References Cited

U.S. PATENT DOCUMENTS

| 6,136,810 | A  | 10/2000 | Takayama et al. |
|---|---|---|---|
| 6,426,365 | B1 | 7/2002  | Shinkai et al. |
| 2005/0059810 | A1 | 3/2005 | Maeda et al. |
| 2006/0178514 | A1 | 8/2006 | Baruah et al. |
| 2006/0270705 | A1 | 11/2006 | Yonemori et al. |
| 2007/0015758 | A1 | 1/2007 | Baruah et al. |
| 2009/0023729 | A1 | 1/2009 | Nakamura et al. |
| 2009/0029994 | A1 | 1/2009 | Nakamura et al. |
| 2009/0062306 | A1 | 3/2009 | Ohgiya et al. |
| 2009/0082352 | A1 | 3/2009 | Ohgiya et al. |

FOREIGN PATENT DOCUMENTS

| EP | 0 885 894 | 12/1998 |
|---|---|---|
| EP | 1 020 439 | 7/2000 |
| JP | 11-49743 | 2/1999 |
| JP | 2003-221376 | 8/2003 |
| WO | 97/19078 | 5/1997 |
| WO | 98/35937 | 8/1998 |
| WO | 00/17164 | 3/2000 |
| WO | 00/17165 | 3/2000 |
| WO | 00/17166 | 3/2000 |
| WO | 03/063868 | 8/2003 |
| WO | 2004/020393 | 3/2004 |
| WO | 2005/095395 | 10/2005 |
| WO | 2006/056854 | 6/2006 |
| WO | 2006/073973 | 7/2006 |
| WO | 2006/098394 | 9/2006 |
| WO | 2007/041494 | 4/2007 |
| WO | 2007/073934 | 7/2007 |
| WO | 2007/075194 | 7/2007 |
| WO | 2007/088996 | 8/2007 |
| WO | 2007/088999 | 8/2007 |
| WO | 2007/126043 | 11/2007 |
| WO | 2007/128568 | 11/2007 |

OTHER PUBLICATIONS

Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
Ulrich, Chapter 4: Crystallization, Kirk-Othmer Encyclopedia of Chemical Technology, Aug. 2002.*
A verified English language translation of U.S. Appl. No. 60/836,948 to Tadaaki Ohgiya et al. filed Aug. 11, 2006.
Usui et al., "A New On-line Enzymatic Method for Simultaneous Quantification of Cholesterol and Triglycerides in Lipoproteins by HPLC,", Journal of Lipid Research vol. 43, pp. 805-814 (2002).

(Continued)

*Primary Examiner*—Deepak Rao
(74) *Attorney, Agent, or Firm*—Greenblum & Bernstein, P.L.C.

(57) ABSTRACT

A compound represented by the following general formula (I) or a salt thereof, or a solvate thereof:

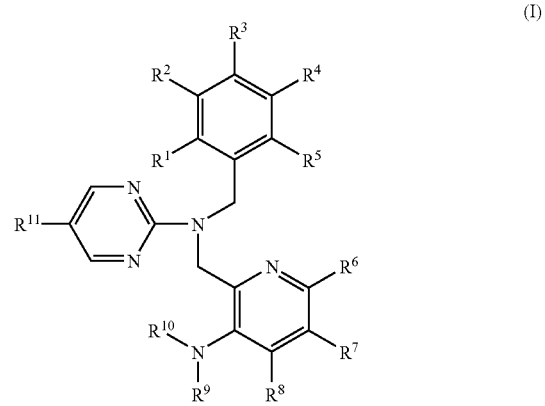

(I)

(wherein $R^1$, $R^2$, $R^3$, $R^4$ and $R^5$ are the same or different, and represent hydrogen atom, a halogen atom, a lower alkyl group etc., $R^6$, $R^7$ and $R^8$ are the same or different, and represent hydrogen atom, a halogen atom, a lower alkyl group etc., $R^9$ and $R^{10}$ are the same or different, and represent hydrogen atom, a lower alkyl group, a (lower cycloalkyl)(lower alkyl) group etc., and $R^{11}$ represents hydrogen atom, a halogen atom, a lower alkoxy group, a (lower alkyl)thio(lower alkoxy) group, a (lower alkyl)sulfinyl(lower alkoxy) group, a (lower alkyl)sulfonyl(lower alkoxy) group etc.), which has potent inhibitory activity on CETP.

6 Claims, No Drawings

OTHER PUBLICATIONS de Grooth, G.J. et al. Efficacy and Safety of a Novel Cholesteryl Ester Transfer Protein Inhibitor, JTT-705, in Humans, *Circulation*, vol. 105, No. 18, pp. 2159-2165 (2002).

Kelly, S.A. et al. A Convergent Approach to Huperzine A and Analogues, *Org. Biomol. Chem.*, vol. 1, No. 16, pp. 2865-2876 (2003).

English language Abstract of JP 2003-221376, (2003).

Fisher, T.H. et al. Meta-Substituent Effects on Benzyl Free-Radical Stability, *J. Org. Chem.*, vol. 55, No. 3, p. 1040-1043 (1990).

U.S. Appl. No. 12/045,982 to Ohgiya et al., filed Mar. 11, 2008.

U.S. Appl. No. 12/100,831 to Ohgiya et al., filed Apr. 10, 2008.

Gomtsyan et al., Bioorganic & Medicinal Chemistry Letters, 2007, vol. 17, pp. 3894-3899.

H. Takahashi et al., Bioorganic & Medicinal Chemistry Letters, 2007, vol. 17, pp. 5091-5095.

English language abstract of JP 11-49743 A, Feb. 23, 1999.

A verified English language translation of U.S. Appl. No. 60/836,948 to Tadaaki Ohgiya et al. filed Aug. 11, 2006.

\* cited by examiner

PYRIMIDINE COMPOUND HAVING BENZYL(PYRIDYLMETHYL)AMINE STRUCTURE AND MEDICAMENT COMPRISING THE SAME

This application claims the benefit of U.S. Provisional Application No. 60/836,948 filed Aug. 11, 2006.

TECHNICAL FIELD

The present invention relates to a novel pyrimidine compound having a benzyl(pyridylmethyl)amine structure and inhibitory activity against cholesterol ester transfer protein (CETP), and a medicament comprising the same.

BACKGROUND ART

In recent years, hyperlipidemia and arteriosclerotic diseases resulting therefrom have been rapidly increasing due to changes into high calorie and high cholesterol-type diet with improvements in living standard, obesity, lack of exercise, aging, and the like. Because a level of low density lipoprotein (LDL) cholesterol and a triglyceride level positively correlate with a risk of onset of heart diseases, conventional pharmacotherapies for hyperlipidemia and arteriosclerosis have been focused on reduction of blood lipids. Whilst, it has been revealed by many researches so far that a level of high density lipoprotein (HDL) cholesterol in plasma negatively correlates with the onset of ischemic heart diseases, and hypo-HDL-emia is considered as one of risk factors of arteriosclerosis. However, no medicament is available at present which selectively and markedly raises an HDL level, and development of such a medicament has been desired.

Cholesterol ester transfer protein (CETP) is an extremely hydrophobic protein which transfers a cholesterol ester from HDL cholesterol to LDL cholesterol, very low density lipoprotein (VLDL) cholesterol or the like, and HDL cholesterol can be increased by inhibiting the transfer by CETP.

Niacin significantly increases HDL cholesterol, but has a serious problem of resistance which reduces compliance. Although fibrates and HMG-CoA reductase inhibitors slightly increase an HDL cholesterol level (10 to 12%), they fail to satisfy medical needs of achieving significant increase of a plasma HDL cholesterol level to delay progress of atherosclerosis. Whilst, the CETP inhibitor attains a potent increase of an HDL cholesterol level, thereby a treatment of hyperlipidemia is achievable with high effectiveness that cannot be exceeded by neither of fibrate or HMG-CoA reductase inhibitors, and thus prophylactic or therapeutic agents for arteriosclerosis or hyperlipidemia, which are conventionally unavailable, are expectedly provided. The CETP inhibitors attain the increase in HDL cholesterol and the decrease in LDL cholesterol or VLDL cholesterol level by a mechanism different from that of HMG-CoA reductase inhibitors, and accordingly, a combinational effect of a CETP inhibitor and a HMG-CoA reductase inhibitor can also be expected.

Several reports have been made so far about compounds to inhibit CETP activity. For example, a thiol derivative which forms a disulfide bond by a reaction with a cysteine residue of CETP to inhibit the CETP activity has been reported (Patent document 1, Non-patent document 1). However, the thiol derivative requires a large amount of administration for expression of the action, and side reactions by formation of disulfide bond with other proteins are concerned.

As CETP inhibitors having a mode of action different from that of the thiol derivative, tetrahydroquinoline derivatives have been disclosed (Patent documents 2 to 4). However, these derivatives are highly liposoluble compounds, and due to low oral absorption resulting from the low water-solubility, they require a pharmaceutical means for obtaining a blood level sufficient for expression of the efficacy (Patent document 5).

Further, tetrahydronaphthylidine derivatives are disclosed as compounds having potent CETP inhibitory activities (Patent document 6). Benzylamine derivatives and the like are also disclosed as compounds having potent CETP inhibitory activity. However, they are highly liposoluble compounds in the same manner as the aforementioned tetrahydroquinoline derivatives (Patent documents 7 and 8).

Furthermore, compounds having a benzyl(heterocyclylmethyl)amine structure are disclosed (Patent document 9). However, the pyrimidine compounds of the present invention having a benzyl(pyridylmethyl)amine structure are not described or suggested, and the compounds described in Patent document 9 are found to have insufficient CETP inhibitory activity as specifically shown in test examples described later.

Patent document 1: Japanese Patent Unexamined Publication (Kokai) No. 11-49743

Patent document 2: International Patent Publication WO2000/17164

Patent document 3: International Patent Publication WO2000/17165

Patent document 4: International Patent Publication WO2000/17166

Patent document 5: International Patent Publication WO2003/63868

Patent document 6: International Patent Publication WO2005/095395

Patent document 7: International Patent Publication WO2004/020393

Patent document 8: International Patent Publication WO2006/056854

Patent document 9: International Patent Publication WO2006/073973

Non-patent document 1: Circulation, 105(18), 2159-2165 (2002)

DISCLOSURE OF THE INVENTION

Therefore, an object of the present invention is to provide a novel compound having a potent inhibitory activity against CETP.

The inventors of the present invention conducted various researches to achieve the aforementioned object. As a result, they found that pyrimidine compounds having a benzyl(pyridylmethyl)amine structure represented by the following general formula (I) and salts thereof as well as solvates thereof had superior CETP inhibitory activity and achieved the present invention.

The present invention thus provides a compound represented by the following general formula (I):

[Formula 1]

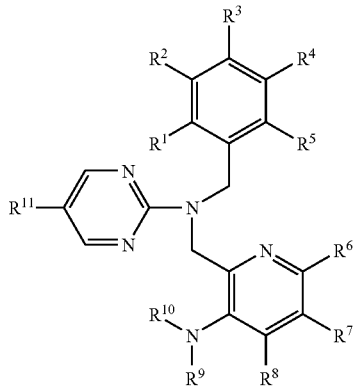

(wherein, $R^1$, $R^2$, $R^3$, $R^4$ and $R^5$ are the same or different, and represent hydrogen atom, a halogen atom, a lower alkyl group, a halo(lower alkyl) group, a lower alkoxy group, a halo(lower alkoxy) group, hydroxy group, cyano group, nitro group, a (lower alkyl)thio group, a (lower alkyl)sulfinyl group, a (lower alkyl)sulfonyl group, sulfonamido group, an amino group which may have a substituent, carboxyl group, a (lower alkyl)carbonyl group, or a (lower alkoxy)carbonyl group, $R^6$, $R^7$ and $R^8$ are the same or different, and represent hydrogen atom, a halogen atom, a lower alkyl group, a lower cycloalkyl group, a (lower cycloalkyl)(lower alkyl) group, a halo(lower alkyl) group, a lower alkoxy group, a halo(lower alkoxy) group, hydroxy group, cyano group, nitro group, a (lower alkyl)thio group, a (lower alkyl)sulfinyl group, a (lower alkyl)sulfonyl group, sulfonamido group, an amino group which may have a substituent, carboxyl group, a (lower alkyl)carbonyl group, or a (lower alkoxy)carbonyl group, $R^9$ and $R^{10}$ are the same or different, and represent hydrogen atom, a lower alkyl group, a (lower cycloalkyl)(lower alkyl) group, an aryl group, an aryl(lower alkyl) group which may have a substituent, or a lower cycloalkyl group, or may combine to form a nitrogen-containing saturated heterocyclic ring together with the adjacent nitrogen atom, and $R^{11}$ represents hydrogen atom, a halogen atom, a lower alkoxy group, a (lower alkyl)thio(lower alkoxy) group, a (lower alkyl)sulfinyl(lower alkoxy) group, a (lower alkyl)sulfonyl(lower alkoxy) group, an aryl(lower alkoxy) group which may have a substituent, a (lower alkyl)amino group, a di(lower alkyl)amino group, a (lower alkyl)thio(lower alkyl)amino group, a (lower alkyl)sulfinyl(lower alkyl)amino group, a (lower alkyl)sulfonyl(lower alkyl)amino group, an arylamino group, a cyclic amino group which may have a hetero atom as a ring-constituting atom, a (lower alkoxy)(lower alkoxy) group, a (lower alkoxy)(lower alkyl)amino group, a hydroxy(lower alkoxy) group, a hydroxy(lower alkyl)amino group, an acylamino group, a (lower alkyl)sulfonylamino group, a hydroxycarbonyl(lower alkoxy) group, an amino(lower alkoxy) group, a (lower alkyl)amino(lower alkoxy) group, or a di(lower alkyl)amino(lower alkoxy) group) or a salt thereof, or a solvate thereof.

The present invention also provides a medicament comprising a compound represented by aforementioned general formula (I) or a salt thereof, or a solvate thereof as an active ingredient, preferably such a medicament for prophylactic and/or therapeutic treatment of diseases including hyperlipidemia, arteriosclerosis, atherosclerosis, peripheral vascular disease, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, diabetic vascular complication, obesity, endotoxemia and the like.

The present invention also provides a CETP inhibitor and an HDL-increasing agent comprising a compound represented by aforementioned general formula (I) or a salt thereof, or a solvate thereof as an active ingredient.

The present invention further provides a pharmaceutical composition comprising a compound represented by the aforementioned general formula (I) or a salt thereof, or a solvate thereof and a pharmaceutically acceptable carrier.

The present invention further provides a method for prophylactic and/or therapeutic treatment of diseases including hyperlipidemia, arteriosclerosis, atherosclerosis, peripheral vascular disease, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, diabetic vascular complication, obesity, endotoxemia and the like, which comprises administering a compound represented by the aforementioned general formula (I) or a salt thereof, or a solvate thereof.

The present invention further provides use of a compound represented by the aforementioned general formula (I) or a salt thereof, or a solvate thereof for the manufacture of the medicament for prophylactic and/or therapeutic treatment of diseases including hyperlipidemia, arteriosclerosis, atherosclerosis, peripheral vascular disease, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, diabetic vascular complication, obesity, endotoxemia and the like.

The present invention further provides a medicament comprising a combination of (a) a compound represented by the aforementioned general formula (I) or a salt thereof, or a solvate thereof and (b) an HMG-CoA reductase inhibitor, preferably such a medicament for prophylactic and/or therapeutic treatment of diseases including hyperlipidemia, arteriosclerosis, atherosclerosis, peripheral vascular disease, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, diabetic vascular complication, obesity, endotoxemia and the like.

The compound of the present invention or a salt thereof, or a solvate thereof exhibits potent inhibitory activity against CETP, as specifically demonstrated in the test examples mentioned later, and can be suitably used as an active ingredient of a CETP inhibitor, further as an active ingredient of an HDL-increasing agent. Furthermore, due to the elevating action on blood HDL cholesterol level thereof on the basis of the CETP inhibitory activity, the compound can be suitably used as an active ingredient of a medicament, more specifically a medicament for prophylactic and/or therapeutic treatment of diseases including hyperlipidemia, arteriosclerosis, atherosclerosis, peripheral vascular disease, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, diabetic vascular complication, obesity, endotoxemia and the like.

Moreover, the compound of the present invention or a salt thereof, or a solvate thereof has a superior feature that the compound is capable of exerting potent inhibitory activity on CETP by oral administration.

BEST MODE OF CARRYING OUT THE INVENTION

Examples of the lower alkyl group moiety of the lower alkyl group, the halo(lower alkyl) group, the (lower cycloalkyl)(lower alkyl) group, and the aryl(lower alkyl) group referred to in the present invention include a linear or branched alkyl group having 1 to 6 carbon atoms (referred to as $C_1$-$C_6$ alkyl), for example, methyl, ethyl, n-propyl, isopropyl, n-butyl, isobutyl, t-butyl, n-pentyl, 2-methylbutyl, 2,2-dimethylpropyl and the like.

Examples of the lower alkoxy group moiety of the lower alkoxy group, the halo(lower alkoxy) group, the (lower alkyl)thio(lower alkoxy) group, the (lower alkyl)sulfinyl(lower alkoxy) group, the (lower alkyl)sulfonyl(lower alkoxy) group, the aryl(lower alkoxy) group, the (lower alkoxy)(lower alkoxy) group, the (lower alkoxy)(lower alkyl)amino group, the hydroxy(lower alkoxy) group, the hydroxycarbonyl(lower alkoxy) group, the amino(lower alkoxy) group, the (lower alkyl)amino(lower alkoxy) group, and the di(lower alkyl)amino(lower alkoxy) group referred to in the present invention include a linear or branched alkoxy group having 1 to 6 carbon atoms (referred to as $C_1$-$C_6$ alkoxy), for example, methoxy, ethoxy, n-propoxy, isopropoxy, n-butoxy, isobutoxy, t-butoxy, n-pentyloxy, 2-methylbutoxy, 2,2-dimethylpropoxy and the like.

Examples of the (lower alkyl)thio group moiety of the (lower alkyl)thio group, the (lower alkyl)thio(lower alkoxy) group and the (lower alkyl)thio(lower alkyl)amino group referred to in the present invention include a linear or branched alkylthio group having 1 to 6 carbon atoms (referred to as ($C_1$-$C_6$ alkyl)thio), for example, methylthio, ethylthio, n-propylthio, isopropylthio, n-butylthio, isobutylthio, t-butylthio, n-pentylthio, 2-methylbutylthio, 2,2-dimethylpropylthio and the like.

Examples of the (lower alkyl)sulfinyl group moiety of the (lower alkyl)sulfinyl group, the (lower alkyl)sulfinyl(lower alkoxy) group, and the (lower alkyl)sulfinyl(lower alkyl)amino group referred to in the present invention include a linear or branched alkylsulfinyl group having 1 to 6 carbon atoms (referred to as ($C_1$-$C_6$ alkyl)sulfinyl), for example, methylsulfinyl, ethylsulfinyl, n-propylsulfinyl, isopropylsulfinyl, n-butylsulfinyl, isobutylsulfinyl, t-butylsulfinyl, n-pentylsulfinyl, 2-methylbutylsulfinyl, 2,2-dimethylpropylsulfinyl and the like.

Examples of the (lower alkyl)sulfonyl group moiety of the (lower alkyl)sulfonyl group, the (lower alkyl)sulfonyl(lower alkoxy) group and the (lower alkyl)sulfonyl(lower alkyl)amino group referred to in the present invention include a linear or branched alkylsulfonyl group having 1 to 6 carbon atoms (referred to as ($C_1$-$C_6$ alkyl)sulfonyl), for example, methylsulfonyl, ethylsulfonyl, n-propylsulfonyl, isopropylsulfonyl, n-butylsulfonyl, isobutylsulfonyl, t-butylsulfonyl, n-pentylsulfonyl, 2-methylbutylsulfonyl, 2,2-dimethylpropylsulfonyl and the like.

Examples of the (lower alkyl)carbonyl group referred to in the present invention include a linear or branched alkylcarbonyl group having 2 to 6 carbon atoms (referred to as ($C_2$-$C_6$ alkyl)carbonyl), for example, methylcarbonyl, ethylcarbonyl, n-propylcarbonyl, isopropylcarbonyl, n-butylcarbonyl, isobutylcarbonyl, t-butylcarbonyl, n-pentylcarbonyl, 2-methylbutylcarbonyl, 2,2-dimethylpropylcarbonyl and the like.

Examples of the (lower alkoxy)carbonyl group moiety of the (lower alkoxy)carbonyl group referred to in the present invention include a linear or branched alkoxycarbonyl group having 2 to 6 carbon atoms (referred to as ($C_2$-$C_6$ alkoxy)carbonyl), for example, methoxycarbonyl, ethoxycarbonyl, n-propoxycarbonyl, isopropoxycarbonyl, n-butoxycarbonyl, isobutoxycarbonyl, t-butoxycarbonyl, n-pentyloxycarbonyl, 2-methylbutoxycarbonyl, 2,2-dimethylpropoxycarbonyl and the like.

Examples of the acylamino group referred to in the present invention include a linear or branched acylamino group having 2 to 6 carbon atoms (referred to as ($C_2$-$C_6$ acyl)amino), for example, acetylamino, n-propionylamino, isopropionylamino, butyrylamino, isobutyrylamino, n-pentanoylamino, 2-methylbutyrylamino, 2,2-dimethylpropionylamino and the like.

Examples of the (lower alkyl)amino group moiety of the (lower alkyl)amino group, the (lower alkyl)thio(lower alkyl) amino group, the (lower alkyl)sulfinyl(lower alkyl)amino group, the (lower alkyl)sulfonyl(lower alkyl)amino group, the (lower alkoxy)(lower alkyl)amino group, the hydroxy (lower alkyl)amino group, and the (lower alkyl)amino(lower alkoxy) group referred to in the present invention include a linear or branched alkylamino group having 1 to 6 carbon atoms (referred to as ($C_1$-$C_6$ alkyl)amino), for example, methylamino, ethylamino, n-propylamino, isopropylamino, n-butylamino, isobutylamino, t-butylamino, n-pentylamino, 2-methylbutylamino, 2,2-dimethylpropylamino and the like.

Examples of the di(lower alkyl)amino group moiety of the di(lower alkyl)amino group and the di(lower alkyl)amino (lower alkoxy) group referred to in the present invention include an amino group substituted with two linear or branched alkyl groups each having 1 to 6 carbon atoms, which may be the same or different (referred to as di($C_1$-$C_6$ alkyl) amino), for example, (ethyl)(methyl)amino, (isopropyl)(n-propyl)amino, (n-butyl)(isobutyl)amino, (t-butyl)(n-pentyl) amino, (2,2-dimethylpropyl)(2-methylbutyl)amino and the like.

Examples of the (lower alkyl)sulfonylamino group moiety of the (lower alkyl)sulfonylamino group referred to in the present invention include a linear or branched alkylsulfonylamino group having 1 to 6 carbon atoms (referred to as ($C_1$-$C_6$ alkyl)sulfonylamino), for example, methylsulfonylamino, ethylsulfonylamino, n-propylsulfonylamino, isopropylsulfonylamino, n-butylsulfonylamino, isobutylsulfonylamino, t-butylsulfonylamino, n-pentylsulfonylamino, 2-methylbutylsulfonylamino, 2,2-dimethylpropylsulfonylamino and the like.

Examples of the lower cycloalkyl group moiety of the lower cycloalkyl group and the (lower cycloalkyl)(lower alkyl) group referred to in the present invention include a cycloalkyl group having 3 to 8 carbon atoms (referred to as $C_3$-$C_8$ cycloalkyl), for example, cyclopropyl, cyclobutyl, cyclopentyl, cyclohexyl and the like.

Examples of the aryl group moiety of the aryl group, the aryl(lower alkyl) group, the aryl(lower alkoxy) group, and the arylamino group referred to in the present invention include an aryl group having 6 to 10 carbon atoms (referred to as $C_6$-$C_{10}$ aryl), for example, phenyl, naphthyl and the like.

Examples of the halogen atom as the halogen atom or the halogen atom of the halo(lower alkyl) group and the halo (lower alkoxy) group referred to in the present invention include fluorine atom, chlorine atom, bromine atom, iodine atom and the like.

In the general formula (I), examples of the lower alkyl group as $R^1$, $R^2$, $R^3$, $R^4$ and $R^5$ include, for example, a $C_1$-$C_6$ alkyl group such as methyl group, ethyl group and n-propyl group, a $C_1$-$C_4$ alkyl group is more preferred, and methyl group is particularly preferred.

In the general formula (I), examples of the lower alkoxy group as $R^1$, $R^2$, $R^3$, $R^4$ and $R^5$ include, for example, a $C_1$-$C_6$ alkoxy group such as methoxy group, ethoxy group and n-propoxy group, a $C_1$-$C_4$ alkoxy group is more preferred, and methoxy group is particularly preferred.

In the general formula (I), examples of the halo(lower alkyl) group as $R^1$, $R^2$, $R^3$, $R^4$ and $R^5$ include, for example, a $C_1$-$C_6$ alkyl group substituted with 1 to 6 halogen atoms such as trifluoromethyl group and pentafluoroethyl group, a $C_1$-$C_4$ alkyl group substituted with 1 to 6 halogen atoms is preferred, and trifluoromethyl group is particularly preferred.

In the general formula (I), examples of the halo(lower alkoxy) group as $R^1$, $R^2$, $R^3$, $R^4$ and $R^5$ include, for example, a $C_1$-$C_6$ alkoxy group substituted with 1 to 6 halogen atoms such as trifluoromethoxy group and pentafluoroethoxy group, a $C_1$-$C_4$ alkoxy group substituted with 1 to 6 halogen atoms is preferred, and trifluoromethoxy group is particularly preferred.

In the general formula (I), examples of the substituent of the amino group which may have a substituent as $R^1$, $R^2$, $R^3$, $R^4$ and $R^5$ include, for example, a lower alkyl group, a halo (lower alkyl) group, an aryl group and the like, and the amino group may have 1 or 2 of these substituents. When the amino group has plural substituents, those substituents may be the same or different.

As for $R^1$, $R^2$, $R^3$, $R^4$ and $R^5$ in the general formula (I), it is preferred that each group, the same or different, is hydrogen atom, a halogen atom, a $C_1$-$C_6$ alkyl group, a halo($C_1$-$C_6$ alkyl) group, a $C_1$-$C_6$ alkoxy group, a halo($C_1$-$C_6$ alkoxy) group, or cyano group, it is more preferred that each group, the same or different, is hydrogen atom, a halo($C_1$-$C_6$ alkyl) group, or cyano group, and it is particularly preferred that each group, the same or different, is hydrogen atom, trifluoromethyl group, or cyano group.

From another aspect, as for $R^1$, $R^2$, $R^3$, $R^4$ and $R^5$, it is preferred that $R^1$, $R^3$ and $R^5$ are hydrogen atoms, and each of $R^2$ and $R^4$, the same or different, is a halo($C_1$-$C_6$ alkyl) group, or cyano group, and it is particularly preferred that $R^1$, $R^3$ and $R^5$ are hydrogen atoms, and each of $R^2$ and $R^4$, the same or different, is trifluoromethyl group, or cyano group.

In the general formula (I), examples of the lower alkoxy group as $R^6$, $R^7$ and $R^8$ include, for example, a $C_1$-$C_6$ alkoxy group such as methoxy group, ethoxy group and n-propoxy group, a $C_1$-$C_4$ alkoxy group is more preferred, and methoxy group is particularly preferred.

In the general formula (I), examples of the substituent of the optionally substitutable amino group as $R^6$, $R^7$ and $R^8$ include, for example, a lower alkyl group, a halo(lower alkyl) group, an aryl group and the like, and the amino group may have 1 or 2 of these substituents. When the amino group has plural substituents, those substituents may be the same or different.

In the general formula (I), as for $R^6$, $R^7$ and $R^8$, it is preferred that each group, the same or different, is hydrogen atom, a $C_1$-$C_6$ alkoxy group, or hydroxy group, it is more preferred that each group, the same or different, is hydrogen atom, or a $C_1$-$C_6$ alkoxy group, and it is particularly preferred that each group, the same or different, is hydrogen atom, or methoxy group.

From another aspect, as for $R^6$, $R^7$ and $R^8$, it is preferred that $R^6$ is a $C_1$-$C_6$ alkoxy group, or hydroxy group, and $R^7$ and $R^8$ are hydrogen atoms, it is more preferred that $R^6$ is a $C_1$-$C_6$ alkoxy group, and $R^7$ and $R^8$ are hydrogen atoms, and it is particularly preferred that $R^6$ is methoxy group, and $R^7$ and $R^8$ are hydrogen atoms.

In the general formula (I), examples of the lower alkyl group as $R^9$ and $R^{10}$ include, for example, a $C_1$-$C_6$ alkyl group such as methyl group, ethyl group, and n-propyl group, a $C_1$-$C_4$ alkyl group is more preferred, and ethyl group is particularly preferred.

In the general formula (I), examples of the (lower cycloalkyl)(lower alkyl) group as $R^9$ and $R^{10}$ include, for example, a ($C_3$-$C_8$ cycloalkyl)($C_1$-$C_6$ alkyl) group such as cyclopropylmethyl group and cyclopentylmethyl group, a ($C_3$-$C_6$ cycloalkyl)($C_1$-$C_4$ alkyl) group is more preferred, and cyclopentylmethyl group is particularly preferred.

In the general formula (I), examples of the nitrogen-containing saturated heterocyclic ring formed by combined $R^9$ and $R^{10}$ together with the adjacent nitrogen atom include, for example, pyrrolidinyl group, piperidinyl group, morpholinyl group, N-(lower alkyl)piperazinyl group and the like.

In the general formula (I), examples of the substituent of the aryl(lower alkyl) group which may have a substituent as $R^9$ and $R^{10}$ include, for example, a halogen atom, a lower alkyl group, a halo(lower alkyl) group, a lower alkoxy group, a halo(lower alkoxy) group, cyano group and the like, and the aryl(lower alkyl) group may have 1 or 2 of these substituents. When the aryl(lower alkyl) group has plural substituents, those substituents may be the same or different. Further, although the substitution positions of these substituents are not particularly limited, they are preferably substitute on the aryl group of the aryl(lower alkyl) group in the present invention. Examples of the group include a ($C_6$-$C_{10}$ aryl)($C_1$-$C_6$ alkyl) group which may have a $C_1$-$C_6$ alkoxy group as a substituent on the aryl group, and 4-methoxybenzyl group is preferred.

In the general formula (I), as for $R^9$ and $R^{10}$, it is preferred that each group, the same or different, is a $C_1$-$C_6$ alkyl group, a ($C_3$-$C_8$ cycloalkyl)($C_1$-$C_6$ alkyl) group, or a ($C_6$-$C_{10}$ aryl)($C_1$-$C_6$ alkyl) group which may have a $C_1$-$C_6$ alkoxy group as a substituent on the aryl group, or combine to form pyrrolidinyl group together with the adjacent nitrogen atom, it is more preferred that each group, the same or different, is a ($C_3$-$C_8$cycloalkyl)($C_1$-$C_6$ alkyl) group, or a $C_1$-$C_6$ alkyl group, and it is particularly preferred that each group, the same or different, is cyclopentylmethyl group, or ethyl group.

From another aspect, as for $R^9$ and $R^{10}$, it is preferred that one of $R^9$ and $R^{10}$ is a ($C_3$-$C_8$ cycloalkyl) ($C_1$-$C_6$ alkyl) group, and the other is a $C_1$-$C_6$ alkyl group, and it is particularly preferred that one of $R^9$ and $R^{10}$ is cyclopentylmethyl group, and the other is ethyl group.

In the general formula (I), examples of the (lower alkyl)thio(lower alkoxy) group as $R^{11}$ include, for example, a ($C_1$-$C_6$ alkyl)thio($C_1$-$C_6$ alkoxy) group such as methylthiomethoxy group, 2-methylthioethoxy group, and 3-methylthiopropoxy group, a ($C_1$-$C_4$ alkyl)thio($C_1$-$C_4$ alkoxy) group is more preferred, and 2-methylthioethoxy group is particularly preferred.

In the general formula (I), examples of the (lower alkyl)sulfinyl(lower alkoxy) group as $R^{11}$ include, for example, a ($C_1$-$C_6$ alkyl)sulfinyl($C_1$-$C_6$ alkoxy) group such as methylsulfinylmethoxy group, 2-methylsulfinylethoxy group, and 3-methylsulfinylpropoxy group, a ($C_1$-$C_4$ alkyl)sulfinyl($C_1$-$C_4$ alkoxy) group is more preferred, and 2-methylsulfinylethoxy group is particularly preferred.

In the general formula (I), examples of the (lower alkyl)sulfonyl(lower alkoxy) group as $R^{11}$ include, for example, a ($C_1$-$C_6$ alkyl)sulfonyl($C_1$-$C_6$ alkoxy) group such as methylsulfonylmethoxy group, 2-methylsulfonylethoxy group, and 3-methylsulfonylpropoxy group, a ($C_1$-$C_4$ alkyl)sulfonyl($C_1$-$C_4$) alkoxy) group is more preferred, and 2-methylsulfonylethoxy group is particularly preferred.

In the general formula (I), examples of the cyclic amino group which may have a hetero atom as a ring-constituting atom as $R^{11}$ include, for example, morpholinyl group, and piperidinyl group.

In the general formula (I), examples of the substituent of the aryl(lower alkoxy) group which may have a substituent as $R^{11}$ include, for example, a halogen atom, a lower alkyl group, a halo(lower alkyl) group, cyano group and the like, and the group may have 1 or 2 of these substituents. When the group have plural substituents, these substituents may be the same or different. Further, although the substitution positions of these substituents are not particularly limited, they preferably substitute on the aryl group of the aryl(lower alkoxy) group in the present invention. Examples of the group include a ($C_6$-$C_{10}$ aryl)($C_1$-$C_6$ alkoxy) group (this ($C_6$-$C_{10}$ alkyl)($C_1$-$C_6$ alkoxy) group may have 1 or 2 substituents selected from a halogen atom, a halo($C_1$-$C_6$ alkyl) group and cyano group as a substituent on the aryl group), and 3-cyano-5-trifluoromethylbenzyloxy group, or 2,3-difluorobenzyloxy group is preferred.

In the general formula (I), $R^{11}$ is preferably a halogen atom, a ($C_1$-$C_6$ alkyl)thio($C_1$-$C_6$ alkoxy) group, a ($C_1$-$C_6$ alkyl)sulfinyl($C_1$-$C_6$ alkoxy) group, a ($C_1$-$C_6$ alkyl)sulfonyl($C_1$-$C_6$ alkoxy) group, a ($C_6$-$C_{10}$ aryl)($C_1$-$C_6$ alkoxy) group (this ($C_6$-$C_{10}$ aryl)($C_1$-$C_6$ alkoxy) group may have 1 or 2 substituents selected from a halogen atom, a halo($C_1$-$C_6$ alkyl) group and cyano group as a substituent on the aryl group), morpholinyl group, or piperidinyl group, more preferably a ($C_1$-$C_6$ alkyl)thio($C_1$-$C_6$ alkoxy) group, a ($C_1$-$C_6$ alkylsulfinyl($C_1$-$C_6$ alkoxy) group, or a ($C_1$-$C_6$ alkyl)sulfonyl($C_1$-$C_6$ alkoxy) group, particularly preferably 2-methylthioethoxy group, 2-methylsulfinylethoxy group, or 2-methylsulfonylethoxy group.

As for preferred combinations of the substituents in the aforementioned general formula (I), it is preferred that each of $R^1$, $R^2$, $R^3$, $R^4$ and $R^5$, the same or different, is hydrogen atom, a halogen atom, a $C_1$-$C_6$ alkyl group, a halo($C_1$-$C_6$ alkyl) group, a $C_1$-$C_6$ alkoxy group, a halo($C_1$-$C_6$ alkoxy) group, or cyano group, each of $R^6$, $R^7$ and $R^8$, the same or different, is hydrogen atom, a $C_1$-$C_6$ alkoxy group, or hydroxy group, each of $R^9$ and $R^{10}$, the same or different, is a $C_1$-$C_6$ alkyl group, a ($C_3$-$C_8$ cycloalkyl)($C_1$-$C_6$ alkyl) group, or a ($C_6$-$C_{10}$ aryl)($C_1$-$C_6$ alkyl) group which may have a $C_1$-$C_6$ alkoxy group on the aryl group as a substituent, or combine to form pyrrolidinyl group together with the adjacent nitrogen atom, and $R^{11}$ is a halogen atom, a ($C_1$-$C_6$ alkyl)thio($C_1$-$C_6$ alkoxy) group, a ($C_1$-$C_6$ alkylsulfinyl($C_1$-$C_6$ alkoxy) group, a ($C_1$-$C_6$ alkyl)sulfonyl($C_1$-$C_6$ alkoxy) group, a ($C_6$-$C_{10}$ aryl)($C_1$-$C_6$ alkoxy) group (this ($C_6$-$C_{10}$ aryl)($C_1$-$C_6$ alkoxy) group may have 1 or 2 substituents selected from a halogen atom, a halo($C_1$-$C_6$ alkyl) group and cyano group on the aryl group as a substituent), morpholinyl group, or piperidinyl group, it is more preferred that each of $R^1$, $R^2$, $R^3$, $R^4$ and $R^5$, the same or different, is hydrogen atom, a halo($C_1$-$C_6$ alkyl) group, or cyano group, each of $R^6$, $R^7$ and $R^8$, the same or different, is hydrogen atom, a $C_1$-$C_6$ alkoxy group, or hydroxy group, each of $R^9$ and $R^{10}$, the same or different, is a ($C_3$-$C_8$ cycloalkyl)($C_1$-$C_6$ alkyd group, or a $C_1$-$C_6$ alkyl group, and $R^{11}$ is a ($C_1$-$C_6$ alkyl)thio($C_1$-$C_6$ alkoxy) group, a ($C_1$-$C_6$ alkyl)sulfinyl($C_1$-$C_6$ alkoxy) group, or a ($C_1$-$C_6$ alkyl)sulfonyl($C_1$-$C_6$ alkoxy) group, and it is particularly preferred that each of $R^1$, $R^2$, $R^3$, $R^4$ and $R^5$, the same or different, is hydrogen atom, trifluoromethyl group, or cyano group, each of $R^6$, $R^7$ and $R^8$, the same or different, is hydrogen atom, or methoxy group, each of $R^9$ and $R^{10}$, the same or different, is cyclopentylmethyl group, or ethyl group, and $R^1$ is 2-methylthioethoxy group, 2-methylsulfinylethoxy group, or 2-methylsulfonylethoxy group.

From another aspect, as for preferred combinations of the substituents, it is preferred that $R^1$, $R^3$ and $R^5$ are hydrogen atoms, each of $R^2$ and $R^4$, the same or different, is a halo($C_1$-$C_6$ alkyl) group, or cyano group, $R^6$ is a $C_1$-$C_6$ alkoxy group, $R^7$ and $R^8$ are hydrogen atoms, one of $R^9$ and $R^{10}$ is a ($C_3$-$C_8$ cycloalkyl)($C_1$-$C_6$ alkyl) group, and the other is a $C_1$-$C_6$ alkyl group, and $R^{11}$ is a ($C_1$-$C_6$ alkyl)thio($C_1$-$C_6$ alkoxy) group, a ($C_1$-$C_6$ alkyl)sulfinyl($C_1$-$C_6$ alkoxy) group, or a ($C_1$-$C_6$ alkyl)sulfonyl($C_1$-$C_6$ alkoxy) group, and it is particularly preferred that $R^1$, $R^3$ and $R^5$ are hydrogen atoms, each of $R^2$ and $R^4$, the same or different, is trifluoromethyl group, or cyano group, $R^6$ is methoxy group, $R^7$ and $R^8$ are hydrogen atoms, one of $R^9$ and $R^{10}$ is cyclopentylmethyl group, and the other is ethyl group, and $R^{11}$ is 2-methylthioethoxy group, 2-methylsulfinylethoxy group, or 2-methylsulfonylethoxy group.

Specific examples of the compound of the present invention represented by the general formula (I) include:

2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine (Example 1), 2-[N-[3-(N-cyclopentylmethyl-N-ethyl)amino-6-methoxypyridin-2-yl]methyl-N-(3-trifluoromethylbenzyl)]amino-5-(2-methylsulfinylethoxy)pyrimidine (Example 2), 2-[N-[3-(N-cyclopentylmethyl-N-ethyl)amino-6-methoxypyridin-2-yl]methyl-N-(3-trifluoromethylbenzyl)]amino-5-(2-methylsulfonylethoxy)pyrimidine (Example 3), 2-[N-benzyl-N-[3-(N-cyclopentylmethyl-N-ethyl)amino-6-methoxypyridin-2-yl]methyl]amino-5-(2-methylthioethoxy)pyrimidine (Example 4), 2-[N-benzyl-N-[3-(N-cyclopentylmethyl-N-ethyl)amino-6-methoxypyridin-2-yl]methyl]amino-5-(2-methylsulfinylethoxy)pyrimidine (Example 5), 2-[N-benzyl-N-[3-(N-cyclopentylmethyl-N-ethyl)amino-6-methoxypyridin-2-yl]methyl]amino-5-(2-methylsulfonylethoxy)pyrimidine (Example 6), 2-[N-(3-cyano-5-trifluoromethylbenzyl)-N-[3-(N-cyclopentylmethyl-N-ethyl)amino-6-methoxypyridin-2-yl]methyl]amino-5-(2-methylthioethoxy)pyrimidine (Example 7), 2-[N-(3-cyano-5-trifluoromethylbenzyl)-N-[3-(N-cyclopentylmethyl-N-ethyl)amino-6-methoxypyridin-2-yl]methyl]amino-5-(3-cyano-5-trifluoromethylbenzyloxy)pyrimidine (Example 8), 2-[N-(3-cyano-5-trifluoromethylbenzyl)-N-[3-(N-cyclopentylmethyl-N-ethyl)amino-6-methoxypyridin-2-yl]methyl]amino-5-(2-methylsulfinylethoxy)pyrimidine (Example 9), 2-[N-(3-cyano-5-trifluoromethylbenzyl)-N-[3-(N-cyclopentylmethyl-N-ethyl)amino-6-methoxypyridin-2-yl]methyl]amino-5-(2-methylsulfonylethoxy)pyrimidine (Example 10), 2-[N-[3,5-bis(trifluoromethyl)benzyl]-N-[3-(N-cyclopentylmethyl-N-ethyl)amino-6-methoxypyridin-2-yl]methyl]amino-5-(2-methylthioethoxy)pyrimidine (Example 11), 2-[N-[3,5-bis(trifluoromethyl)benzyl]-N-[3-(N-cyclopentylmethyl-N-ethyl)amino-6-methoxypyridin-2-yl]methyl]amino-5-(2-methylsulfinylethoxy)pyrimidine (Example 12), 2-[N-[3,5-bis(trifluoromethyl)benzyl]-N-[3-(N-cyclopentylmethyl-N-ethyl)amino-6-methoxypyridin-2-yl]methyl]amino-5-(2-methylsulfonylethoxy)pyrimidine (Example 13), 2-[N-(3-cyanobenzyl)-N-[3-(N-cyclopentylmethyl-N-ethyl)amino-6-methoxypyridin-2-yl]methyl]amino-5-(2-methylthioethoxy)pyrimidine (Example 14), 2-[N-(3-cyanobenzyl)-N-[3-(N-cyclopentylmethyl-N-ethyl)amino-6-methoxypyridin-2-yl]methyl]amino-5-(2-methylsulfinylethoxy)pyrimidine (Example 15), 2-[N-[2,5-bis(trifluoromethyl)benzyl]-N-[3-(N-cyclopentylmethyl-N-ethyl)amino-6-methoxypyridin-2-yl]methyl]amino-5-(2-methylthioethoxy)pyrimidine (Example 16), 2-[N-[2,5-bis(trifluoromethyl)benzyl]-N-[3-(N-cyclopentylmethyl-N-ethyl)amino-6-methoxypyridin-2-yl]methyl]amino-5-(2-methylsulfinylethoxy)pyrimidine (Example 17), 2-[N-[3-(N-cyclopentylmethyl-N-ethyl)amino-6-methoxypyridin-2-yl]methyl-N-(3,5-difluorobenzyl)]amino-5-(2-methylthioethoxy)pyrimidine (Example 18), 2-[N-[3-(N-cyclopentylmethyl-N-ethyl)amino-6-methoxypyridin-2-yl]methyl-N-(3,5-difluorobenzyl)]amino-5-(2-methylsulfinylethoxy)pyrimidine (Example 19), 2-[N-[3-(N-cyclopentylmethyl-N-ethyl)amino-6-methoxypyridin-2-yl]methyl-N-(3,5-difluorobenzyl)]amino-5-(2-methylsulfonylethoxy)pyrimidine (Example 20), 2-[N-[3-(N-cyclopentylmethyl-N-ethyl)amino-6-methoxypyridin-2-yl]methyl-N-(3,5-dichlorobenzyl)]amino-5-(2-methylthioethoxy)pyrimidine (Example 21), 2-[N-[3-(N-cyclopentylmethyl-N-ethyl)amino-6-methoxypyridin-2-yl]methyl-N-(3,5-dichlorobenzyl)]amino-5-(2-methylsulfinylethoxy)pyrimidine (Example 22), 2-[N-[3-(N-cyclopentylmethyl-N-ethyl)amino-6-methoxypyridin-2-yl]methyl-N-(3,5-dimethoxybenzyl)]amino-5-(2-methylthioethoxy)pyrimidine (Example 23), 2-[N-[3-(N-cyclopentylmethyl-N-ethyl)amino-6-methoxypyridin-2-yl]methyl-N-(3,5-dimethoxybenzyl)]amino-5-(2-methylsulfinylethoxy)pyrimidine (Example 24), 2-[N-[3-(N-cyclopentylmethyl-N-ethyl)amino-6-methoxypyridin-2-yl]methyl-N-(3,5-dimethoxybenzyl)]amino-5-(2-methylsulfonylethoxy)pyrimidine (Example 25), 2-[N-[3-(N-cyclopentylmethyl-N-ethyl)amino-6-methoxypyridin-2-yl]methyl-N-(3-trifluoromethoxybenzyl)]amino-5-(2-methylthioethoxy)pyrimidine (Example 26), 2-[N-[3-(N-cyclopentylmethyl-N-ethyl)amino-6-methoxypyridin-2-yl]methyl-N-(3-trifluoromethoxybenzyl)]amino-5-(2-methylsulfinylethoxy)pyrimidine (Example 27), 2-[N-[3-(N-cyclopentylmethyl-N-ethyl)amino-6-methoxypyridin-2-yl]methyl-N-(3-trifluoromethoxybenzyl)]amino-5-(2-methylsulfonylethoxy)pyrimidine (Example 28), 2-[N-[3-(N-cyclopentylmethyl-N-ethyl)amino-6-methoxypyridin-2-yl]methyl-N-(3,5-dimethylbenzyl)]amino-5-(2-methylthioethoxy)pyrimidine (Example 29), 2-[N-[3-(N-cyclopentylmethyl-N-ethyl)amino-6-methoxypyridin-2-yl]methyl-N-(3,5-dimethylbenzyl)]amino-5-(2-methylsulfinylethoxy)pyrimidine (Example 30), 2-[N-[3-(N-cyclopentylmethyl-N-ethyl)amino-6-methoxypyridin-2-yl]methyl-N-(3,4-difluorobenzyl)]amino-5-(2-methylthioethoxy)pyrimidine (Example 31), 2-[N-[3-(N-cyclopentylmethyl-N-ethyl)amino-6-methoxypyridin-2-yl]methyl-N-(3,4-difluorobenzyl)]amino-5-(2-methylsulfinylethoxy)pyrimidine (Example 32), 2-[N-[3-(N-cyclopentylmethyl-N-ethyl)amino-6-methoxypyridin-2-yl]methyl-N-(2,5-difluorobenzyl)]amino-5-(2-methylthioethoxy)pyrimidine (Example 33), 2-[N-[3-(N-cyclopentylmethyl-N-ethyl)amino-6-methoxypyridin-2-yl]methyl-N-(2,5-difluorobenzyl)]amino-5-(2-methylsulfinylethoxy)pyrimidine (Example 34), 2-[N-[3-(N-cyclopentylmethyl-N-ethyl)amino-6-methoxypyridin-2-yl]methyl-N-(2,6-difluorobenzyl)]amino-5-(2-methylthioethoxy)pyrimidine (Example 35), 2-[N-[3-(N-cyclopentylmethyl-N-ethyl)amino-6-methoxypyridin-2-yl]methyl-N-(2,6-difluorobenzyl)]amino-5-(2-methylsulfinylethoxy)pyrimidine (Example 36), 2-[N-[3-(N-cyclopentylmethyl-N-ethyl)amino-6-methoxypyridin-2-yl]methyl-N-(2,3-difluorobenzyl)]amino-5-(2-methylthioethoxy)pyrimidine (Example 37), 2-[N-[3-(N-cyclopentylmethyl-N-ethyl)amino-6-methoxypyridin-2-yl]methyl-N-(2,3-difluorobenzyl)]amino-5-(2,3-difluorobenzyloxy)pyrimidine (Example 38), 2-[N-[3-(N-cyclopentylmethyl-N-ethyl)amino-6-methoxypyridin-2-yl]methyl-N-(2,3-difluorobenzyl)]amino-5-(2-methylsulfinylethoxy)pyrimidine (Example 39), 2-[N-[3-(N-cyclopentylmethyl-N-ethyl)amino-6-methoxypyridin-2-yl]methyl-N-(3,6-dicyanobenzyl)]amino-5-(2-methylthioethoxy)pyrimidine (Example 40), 2-[N-[3-(N-cyclopentylmethyl-N-ethyl)amino-6-methoxy-pyridin-2-yl]methyl-N-(3,5-dicyanobenzyl)]amino-5-(2-methylsulfinylethoxy)pyrimidine (Example 41), 2-[N-[3-(N-cyclopentylmethyl-N-ethyl)amino-6-methoxy-pyridin-2-yl]methyl-N-(3,5-dicyanobenzyl)]amino-5-(2-methylsulfonylethoxy)pyrimidine (Example 42), 2-[N-[3-(N-cyclopentylmethyl-N-ethyl)amino-6-methoxy-pyridin-2-yl]methyl-N-(4-trifluoromethylbenzyl)]amino-5-(2-methylthioethoxy)pyrimidine (Example 43), 2-[N-[3-(N-cyclopentylmethyl-N-ethyl)amino-6-methoxy-pyridin-2-yl]methyl-N-(4-trifluoromethylbenzyl)]amino-5-(2-methylsulfinylethoxy)pyrimidine (Example 44), 2-[N-[3-(N-cyclopentylmethyl-N-ethyl)amino-6-methoxy-pyridin-2-yl]methyl-N-(4-trifluoromethylbenzyl)]amino-5-(2-methylsulfonylethoxy)pyrimidine (Example 45), 2-[N-[3,5-bis(trifluoromethyl)benzyl]-N-[3-(N-cyclopentylmethyl-N-ethyl)amino-6-methoxypyridin-2-yl]methyl]amino-5-bromopyrimidine (Example 46), 2-[N-[3,5-bis(trifluoromethyl)benzyl]-N-[3-(N-cyclopentylmethyl-N-ethyl)amino-6-methoxypyridin-2-yl]methyl]amino-5-(4-morpholino)pyrimidine (Example 47), 2-[N-[3,5-bis(trifluoromethyl)benzyl]-N-[3-(N-cyclopentylmethyl-N-ethyl)amino-6-methoxypyridin-2-yl]methyl]amino-5-(piperidin-1-yl)pyrimidine (Example 48), 2-[N-[3,5-bis(trifluoromethyl)benzyl]-N-[6-methoxy-3-(pyrrolidin-1-yl)pyridin-2-yl]methyl]amino-5-(2-methylthioethoxy)pyrimidine (Example 49), 2-[N-[3,5-bis(trifluoromethyl)benzyl]-N-[6-methoxy-3-(pyrrolidin-1-yl)pyridin-2-yl]methyl]amino-5-(2-methylsulfinylethoxy)pyrimidine (Example 50), 2-[N-[3,5-bis(trifluoromethyl)benzyl]-N-[6-methoxy-3-(pyrrolidin-1-yl)pyridin-2-yl]methyl]amino-5-(2-methylsulfonylethoxy)pyrimidine (Example 51), 2-[N-[3,5-bis(trifluoromethyl)benzyl]-N-[3-(cyclopentylmethyl)ethylamino-6-hydroxypyridin-2-yl]methyl]amino-5-(2-methylsulfonylethoxy)pyrimidine (Example 52), 2-[N-(4-cyanobenzyl)-N-[3-(N-cyclopentylmethyl-N-ethyl)amino-6-methoxypyridin-2-yl]methyl]amino-5-(2-methylthioethoxy)pyrimidine (Example 53), 2-[N—[N-(4-cyanobenzyl)-3-(N-cyclopentylmethyl-N-ethyl)amino-6-methoxypyridin-2-yl]methyl]amino-5-(2-methylsulfinylethoxy)pyrimidine (Example 54), and 2-[N-[3,5-bis(trifluoromethyl)benzyl]-N-[3-[N-ethyl-N-(4-methoxybenzyl)]amino-6-methoxypyridin-2-yl]methyl]amino-5-(2-methylthioethoxy)pyrimidine (Example 55), and preferred are:

2-[N-(3-cyano-5-trifluoromethylbenzyl)-N-[3-(N-cyclopentylmethyl-N-ethyl)amino-6-methoxypyridin-2-yl]methyl]amino-5-(2-methylsulfinylethoxy)pyrimidine (Example 9), 2-[N-(3-cyano-5-trifluoromethylbenzyl)-N-[3-(N-cyclopentylmethyl-N-ethyl)amino-6-methoxypyridin-2-yl]methyl]amino-5-(2-methylsulfonylethoxy)pyrimidine (Example 10), 2-[N-[3,5-bis(trifluoromethyl)benzyl]-N-[3-(N-cyclopentylmethyl-N-ethyl)amino-6-methoxypyridin-2-yl]methyl]amino-5-(2-methylsulfinylethoxy)pyrimidine (Example 12), 2-[N-[3,5-bis(trifluoromethyl)benzyl]-N-[3-(N-cyclopentylmethyl-N-ethyl)amino-6-methoxypyridin-2-yl]methyl]amino-5-(2-methylsulfonylethoxy)pyrimidine (Example 13), 2-[N-[3-(N-cyclopentylmethyl-N-ethyl)amino-6-methoxy-pyridin-2-yl]methyl-N-(3,5-dicyanobenzyl)]amino-5-(2-methylsulfinylethoxy)pyrimidine (Example 41), and 2-[N-[3-(N-cyclopentylmethyl-N-ethyl)amino-6-methoxy-pyridin-2-yl]methyl-N-(3,5-dicyanobenzyl)]amino-5-(2-methylsulfonylethoxy)pyrimidine (Example 42).

The compound of the present invention represented by the general formula (I) can be prepared by various known methods, which methods are not particularly limited. For example, the compound can be prepared according to the following reaction steps, but the method for preparation is not limited thereto. Further, when the following reactions are performed, functional groups other than the reaction sites may be protected beforehand as required, and deprotected in an appropriate stage. Furthermore, each reaction may be performed by an ordinarily used method in each step, and isolation and purification can be performed by a means suitably selected from conventional methods such as crystallization, recrystallization, chromatography and the like, or a combination thereof.

More specifically, as shown in the following reaction scheme 1, by protecting the hydroxy group of a 2-hydroxymethylpyridine derivative represented by the general formula (II) with a protective group $R^{12}$, a compound represented by the general formula (III) can be obtained. The protective group $R^{12}$ in the general formula (III) is a protective group generally used as a protective group of hydroxy group. Although the group is not particularly limited, preferred examples include methoxymethyl group, benzyloxymethyl group, 4-methoxybenzyloxymethyl group, methoxyethoxymethyl group, ethoxyethyl group, t-butyldimethylsilyl group, triethylsilyl group, t-butyldiphenylsilyl group, triisopropylsilyl group, triphenylsilyl group, 4-methoxybenzyl group, benzyl group, 3,4-dimethoxybenzyl group, 2,4,6-trimethylbenzyl group, trityl group and the like. By reacting the compound represented by the general formula (III) and an amine represented by the general formula (IV), an aminopyridine derivative represented by the general formula (V) can be obtained. By reacting the resulting aminopyridine derivative represented by the general formula (V) with a compound having a leaving group $W^2$ represented by the general formula (VI), or with an aldehyde derivative represented by the general formula (VII) according to a method for reductive amination, an aminopyridine derivative represented by the general formula (VIII) can be obtained.

The protective group $R^{12}$ of the resulting aminopyridine derivative represented by the general formula (VIII) can be removed to obtain an alcohol compound represented by the general formula (IX), and then the produced hydroxy group can be oxidized to obtain an aldehyde derivative represented by the general formula (X). By reacting the resulting aldehyde derivative represented by the general formula (X) with an aminopyrimidine derivative represented by the general formula (XI) according to a method for reductive amination, an amine compound represented by the general formula (XII) can be obtained. By reacting the amine compound represented by the general formula (XII) with a compound having a leaving group $W^3$ represented by the general formula (XIII) with a base, a compound of the present invention represented by the general formula (I) can be prepared.

This reaction route is represented by reaction formulas as follows.

Reaction scheme 1

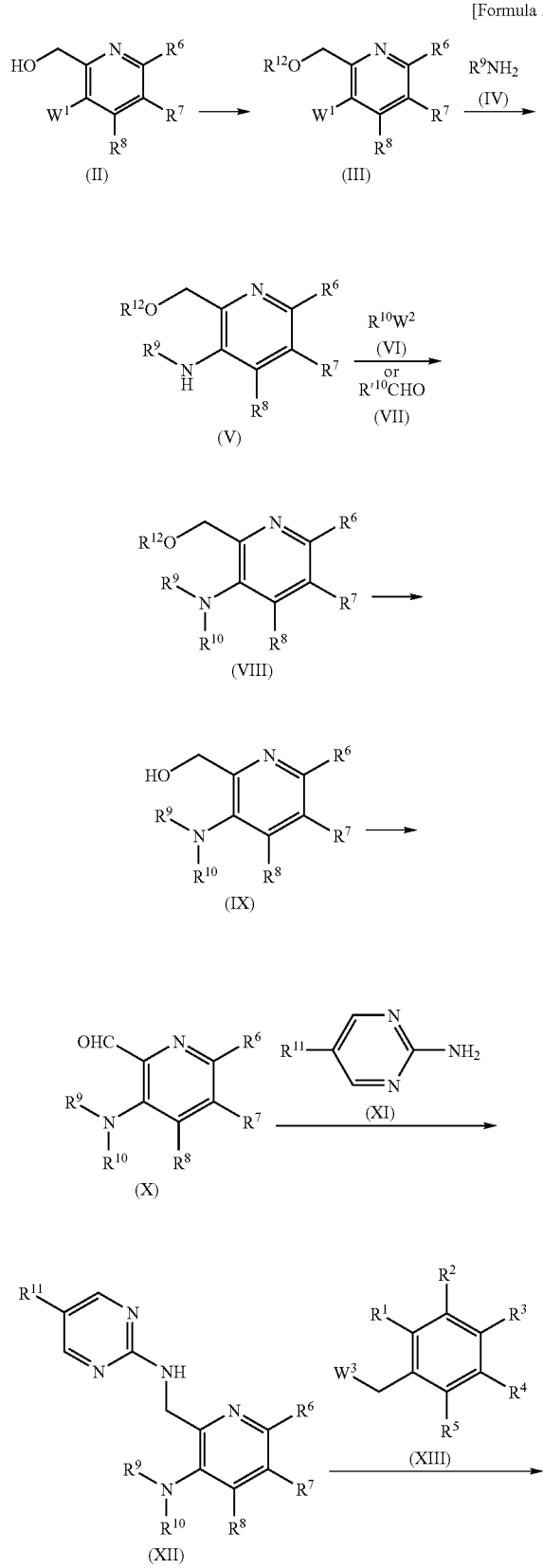

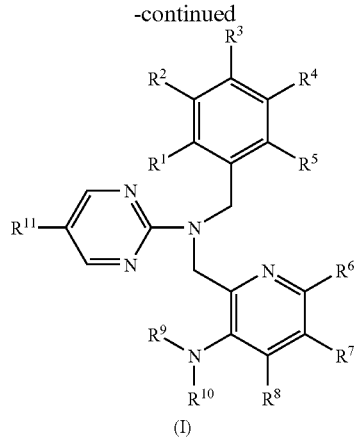

(wherein $R^1$, $R^2$, $R^3$, $R^4$, $R^5$, $R^6$, $R^7$, $R^8$, $R^9$, $R^{10}$ and $R^{11}$ have the same meanings as those explained for the general formula (I) mentioned above, $W^1$, $W^2$ and $W^3$ represent a halogen atom, an alkylsulfonyloxy group, a haloalkylsulfonyloxy group, or an arylsulfonyloxy group, $R^{12}$ represents a protective group, and $R'^{10}$ represents a lower alkyl group, a (lower cycloalkyl)alkyl group or a lower cycloalkyl group, of which number of the carbon atoms at the bond position to the nitrogen atom is smaller than that of $R^{10}$ by 1)

Introduction of the protective group $R^{12}$ into the 2-hydroxymethylpyridine derivative (II) can be attained by referring to a method generally used as a deprotection condition for that protective group (Protective Groups in Organic Synthesis Third Edition, John Wiley & Sons, Inc.).

For the reaction of the resulting compound (III) and the amine (IV), a method for a reaction of an aryl halide and an amine performed in the presence or absence of a base and in the presence of a metal catalyst can be applied. In this reaction, for example, by reacting both of the compounds in a solvent in the presence of a metal catalyst, the target compound can be obtained. During the reaction, microwave irradiation may be performed. As the metal catalyst, for example, tris(dibenzylideneacetone)dipalladium(0), tris(dibenzylideneacetone)(chloroform)dipalladium(0), [1,1'-bis(diphenylphosphino)ferrocene]dichloropalladium(II), tetrakis(triphenylphosphine)palladium and the like may be independently used, but a ligand such as 2-biphenyl(di-t-butylphosphine) and 2-biphenyl(dicyclohexylphosphine) may also be used in combination. As the solvent, although not particularly limited, for example, tetrahydrofuran, toluene, dioxane, N,N-dimethylformamide, N-methylpyrrolidone, water and the like may be used alone or in combination. Further, the amine (IV) may be used as the solvent. Although the base is not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like may be used. As for the reaction conditions, although they should be changed depending on the starting material to be used, the target compound can be obtained by starting the reaction generally at 0 to 180° C., preferably at room temperature under microwave irradiation, elevating the temperature to 80 to 150° C., and performing the reaction for 1 minute to 20 hours, preferably 1 minute to 3 hours, including the temperature elevation time. Further, when microwaves are not irradiated, the target compound can be obtained by performing the reaction at 100 to 180° C., preferably at 100 to 160° C., for 5 minutes to 10 hours, preferably 10 minutes to 5 hours.

The reaction of the aminopyridine derivative (V) obtained in the above reaction and the compound (VI) having a leaving group $W^2$ can be performed in a solvent in the presence of a base. As the solvent, although not particularly limited, for example, N,N-dimethylformamide, N-methylpyrrolidone, dimethyl sulfoxide, dioxane, tetrahydrofuran, acetonitrile, propionitrile and the like can be used. As the base, although not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like may be used.

The reaction of the aminopyridine derivative (V) and the aldehyde derivative (VII) can be performed in a solvent by using a reducing reagent in the presence or absence of an acid. The acid may be used as the solvent. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile, methanol, ethanol, isopropanol, and the like can be used alone or in combination. As the acid, although not particularly limited, for example, proton acids such as acetic acid, trifluoroacetic acid, propionic acid and benzoic acid, and Lewis acids such as titanium tetrachloride, boron trifluoride and stannic chloride can be used. The reducing regent is not particularly limited, and for example, catalytic reduction using a borohydride type regent such as sodium triacetoxyborohydride, tetramethylammonium triacetoxyborohydride, sodium cyanoborohydride, sodium borohydride, lithium borohydride, sodium trimethoxyborohydride and lithium triethylborohydride, or an aluminum hydride regent such as lithium aluminum hydride, diisopropylaluminum hydride and sodium bis(2-methoxyethoxy)aluminum hydride, a metal catalyst and a hydrogen source can be used. For the catalytic reduction, as the hydrogen source, for example, hydrogen, cyclohexadiene, formic acid, ammonium formate and the like can be used, and as the metal catalyst, for example, palladium/carbon, palladium black, palladium hydroxide/carbon powder, Raney nickel, platinum dioxide, platinum black and the like can be used.

The method for removing the protective group $R^{12}$ of the aminopyridine derivative (VIII) obtained by the aforementioned method, although not particularly limited, can be performed by referring to a method generally used for removal of the protective group (Protective Groups in Organic Synthesis Third Edition, John Wiley & Sons, Inc.).

For the oxidation reaction of the alcohol compound (IX), an ordinary method for oxidizing hydroxy group into aldehyde can be applied. For example, oxidation conditions of Swern oxidation, Moffatt oxidation, Dess-Martin oxidation and the like, and pyridinium chlorochromate (PCC), pyridinium dichromate (PDC), manganese dioxide, tetrapropylammonium perruthenate (TPAP) and the like can be used. As the solvent, although not particularly limited, for example, tetrahydrofuran, dichloromethane, chloroform, 1,2-dichloroethane, N,N-dimethylformamide, and the like can be used alone or in combination.

The reaction of the aldehyde derivative (X) obtained by the aforementioned method and the aminopyrimidine derivative (XI) can be performed in a solvent by using a reducing reagent in the presence or absence of an acid. The acid may be used as the solvent. As the solvent, although not particularly limited, for example, 1,2-dichloroethane, chloroform, dichloromethane, ethyl acetate, isopropyl acetate, toluene, benzene, tetrahydrofuran, dioxane, acetonitrile, propionitrile, methanol, ethanol, isopropanol, and the like can be used alone or in combination. As the acid, although not particularly limited, for example, proton acids such as acetic acid, trifluoroacetic acid, propionic acid and benzoic acid, and Lewis acids such as titanium tetrachloride, boron trifluoride and stannic chloride can be used. The reducing regent is not particularly limited, and for example, catalytic reduction using a borohydride regent such as sodium triacetoxyborohydride, tetramethylammonium triacetoxyborohydride, sodium cyanoborohydride, sodium borohydride, lithium borohydride, sodium trimethoxyborohydride and lithium triethylborohydride, or an aluminum hydride regent such as lithium aluminum hydride, diisopropylaluminum hydride, sodium bis(2-methoxyethoxy)aluminum hydride, a metal catalyst and hydrogen source can be used. For the catalytic reduction, as the hydrogen source, for example, hydrogen, cyclohexadiene, formic acid, ammonium formate and the like can be used, and as the metal catalyst, for example, palladium/carbon, palladium black, palladium hydroxide/carbon powder, Raney nickel, platinum dioxide, platinum black and the like can be used.

The reaction of the amine compound (XII) obtained by the method described above and the compound (XIII) having a leaving group $W^3$ can be performed in a solvent in the presence of a base. As the solvent, although not particularly limited, for example, N,N-dimethylformamide, N-methylpyrrolidone, dimethyl sulfoxide, dioxane, tetrahydrofuran, acetonitrile, propionitrile, and the like can be used, and as the base, although not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like may be used.

As the aminopyrimidine derivative (XI) used in the reaction mentioned in the aforementioned reaction scheme 1, an available compound may be used per se, or the derivative can be suitably prepared by a known method. For example, said derivative can be prepared by the following methods. However, the preparation method is not limited to the following example.

The aminopyrimidine derivative wherein $R^{11}$ is a lower alkoxy group, a (lower alkyl)thio(lower alkoxy) group, a di(lower alkyl)amino group, a cyclic amino group which may have a hetero atom as a ring-constituting atom, a (lower alkoxy)(lower alkoxy) group, or a di(lower alkyl)amino (lower alkoxy) group can be prepared by the following methods.

When $R^{11}$ is a lower alkoxy group, a (lower alkyl)thio (lower alkoxy) group, a di(lower alkyl)amino group, a cyclic amino group which may have a hetero atom as a ring-constituting atom, a (lower alkoxy)(lower alkoxy) group, or a di(lower alkyl)amino(lower alkoxy) group, known methods can be used for the preparation of the 2-aminopyrimidine derivative (XI). Examples are mentioned below.

1-1: Method for Preparing Aminopyrimidine Compound (XI') wherein $R^{11}$ is a Di(Lower Alkyl)Amino Group or a Cyclic Amino Group which May have a Hetero Atom as a Ring-Constituting Atom As shown in the following reaction scheme 2, by a reaction of 2-amino-5-bromopyrimidine (XIV) and an amine represented by the general formula (XV), the aminopyrimidine compound represented by the general formula (XI') wherein $R^{11}$ is a di(lower alkyl)amino group or a cyclic amino group which may have a hetero atom as a ring-constituting atom can be obtained.

This reaction route is shown with a reaction scheme as follows.

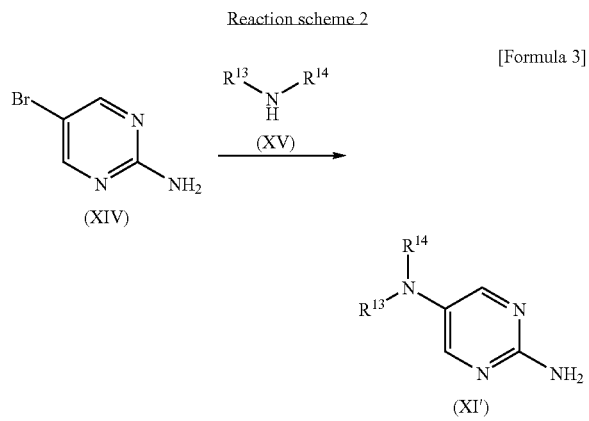

(In the formula, $R^{13}$ and $R^{14}$ are the same or different, and represent a lower alkyl group, or $R^{13}$ and $R^{14}$ combine to form a cyclic amine which may have a hetero atom as a ring-constituting atom together with the nitrogen atom to which they bind)

For the reaction of 2-amino-5-bromopyrimidine (XIV) and the amine (XV), a method for a reaction of an aryl halide and an amine performed in a solvent or without solvent in the presence or absence of a base and in the presence of a metal catalyst can be applied. In this reaction, for example, by reacting both of the compounds in a solvent in the presence of a metal catalyst, the target compound can be obtained. During the reaction, microwave irradiation may be performed. As the metal catalyst, for example, a palladium complex such as tris(dibenzylideneacetone)dipalladium(0), tris(dibenzylideneacetone)(chloroform)dipalladium(0), [1,1'-bis(diphenylphosphino)ferrocene]dichloropalladium(II) and tetrakis(triphenylphosphine)palladium, or a monovalent copper regent such as cuprous iodide, cuprous bromide and cuprous cyanide may be used alone, a ligand such as (2-biphenyl)di-t-butylphosphine, (2-biphenyl)dicyclohexylphosphine, tetramethylethylenediamine, N,N'-dimethylethylenediamine, glycine, N,N-dimethylglycine and N-methylglycine may also be used in combination. As the solvent, although not particularly limited, for example, tetrahydrofuran, toluene, dioxane, N,N-dimethylformamide, N-methylpyrrolidone, dimethyl sulfoxide, water and the like may be used alone or in combination. Although the base is not particularly limited, for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like may be used. As for the reaction conditions, the target compound can be obtained by performing the reaction at 0 to 180° C., preferably 80 to 150° C., for 1 minute to 5 days, preferably 1 hour to 3 days.

1-2: Method for Preparing Aminopyrimidine Compound (XI") wherein $R^{11}$ is a Lower Alkoxy Group, a (Lower Alkyl) Thio(Lower Alkoxy) Group, a (Lower Alkoxy)(Lower Alkoxy) Group or a Di(Lower Alkyl)Amino(Lower Alkoxy) Group As shown in the following reaction scheme 3, by a reaction of 5-bromo-2-chloropyrimidine (XVI) and an amine represented by the general formula (XVII) having a removable functional group $R^{15}$, an aminopyrimidine compound represented by the general formula (XVIII) can be obtained. By a reaction of the resulting aminopyrimidine compound represented by the general formula (XVIII) and an alcohol represented by the general formula (XIX), an ether compound represented by the general formula (XX) can be obtained, and by further removing the functional group $R^{15}$ for deprotection, the aminopyrimidine compound represented by the general formula (XI") wherein $R^{11}$ is a lower alkoxy group, a (lower alkyl)thio(lower alkoxy) group, a (lower alkoxy) (lower alkoxy) group or a di(lower alkyl)amino(lower alkoxy) group can be obtained.

This reaction route is shown with a reaction scheme as follows.

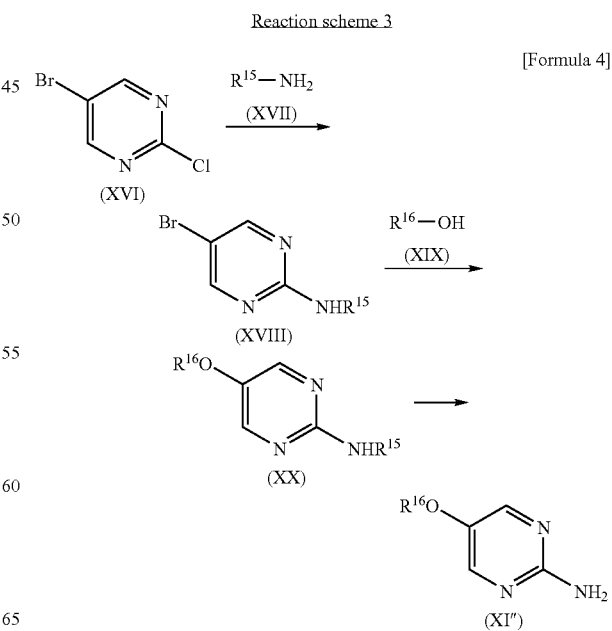

(In the formula, $R^{15}$ represents a protective group, and $R^{16}$ represents a lower alkyl group, a (lower alkyl)thio(lower alkoxy) group, a (lower alkoxy)(lower alkyl) group or a di(lower alkyl)amino(lower alkyl) group)

As for the reaction of 5-bromo-2-chloropyrimidine (XVI) and the amine (XVII), the target compound can be obtained by performing the reaction in a solvent or without solvent. During the reaction, microwave irradiation may be performed. As the solvent, although not particularly limited, for example, tetrahydrofuran, toluene, dioxane, N,N-dimethylformamide, N-methylpyrrolidone, dimethyl sulfoxide, water, and the like can be used alone or in combination. As for the reaction conditions, although they should be changed depending on the amine (XVII) to be used, the target compound can be obtained by performing the reaction generally at −20 to 180° C., preferably 0 to 150° C., for 1 minute to 24 hours, preferably 5 minutes to 10 hours.

For the reaction of the resulting aminopyrimidine compound (XVIII) and the alcohol (XIX), a method for a reaction of an aryl halide and an alcohol performed in a solvent or without solvent in the presence or absence of a base and in the presence of a metal catalyst can be applied. In this reaction, for example, by reacting both of the compounds in a solvent in the presence of a metal catalyst, the target compound can be obtained. During the reaction, microwave irradiation may be performed. As the metal catalyst, for example, a palladium complex such as tris(dibenzylideneacetone)dipalladium(0), tris(dibenzylideneacetone)(chloroform)dipalladium(0), [1,1'-bis(diphenylphosphino)ferrocene]dichloropalladium (II), and tetrakis(triphenylphosphine)palladium, or a monovalent copper regent such as cuprous iodide, cuprous bromide and cuprous cyanide may be used alone, and a ligand such as (2-biphenyl)di-t-butylphosphine, (2-biphenyl)dicyclohexylphosphine, tetramethylethylenediamine, N,N'-dimethylethylenediamine, glycine, N,N-dimethylglycine and N-methylglycine may also be used in combination. As the solvent, although not particularly limited, for example, tetrahydrofuran, toluene, dioxane, N,N-dimethylformamide, N-methylpyrrolidone, dimethyl sulfoxide, water and the like may be used alone or in combination. The base is not particularly limited, and for example, alkali metal hydrides such as lithium hydride, sodium hydride and potassium hydride, alkali metals such as lithium, sodium and potassium, alkali metal hydroxides such as lithium hydroxide, sodium hydroxide and potassium hydroxide, alkali metal carbonates such as lithium carbonate, sodium carbonate, potassium carbonate and cesium carbonate, lithium diisopropylamide, sodium diisopropylamide, potassium diisopropylamide, lithium hexamethyldisilazide, sodium hexamethyldisilazide, potassium hexamethyldisilazide, sodium t-butoxide, potassium t-butoxide, n-butyllithium, s-butyllithium, t-butyllithium and the like may be used. As for the reaction conditions, the target compound can be obtained by performing the reaction at 0 to 180° C., preferably 80 to 150° C., for 1 minute to 5 days, preferably 1 hour to 3 days.

Although the method for removing the protective group $R^{15}$ of the ether compound (XX) obtained by the aforementioned method is not particularly limited, the deprotection can be performed by referring to a method generally used for removal of the protective group (Protective Groups in Organic Synthesis Third Edition, John Wiley & Sons, Inc.).

In addition, the compound of the present invention represented by the general formula (I) wherein $R^{11}$ is a (lower alkyl)sulfinyl(lower alkoxy) group or a (lower alkyl)sulfonyl (lower alkoxy) group can also be prepared according to the following reaction steps. Specifically, such a compound can also be obtained by obtaining a compound of the present invention represented by the general formula (I) wherein $R^{11}$ is a (lower alkyl)thio(lower alkoxy) group by using an aminopyrimidine compound (XI") wherein $R^{11}$ is substituted with a (lower alkyl)thio(lower alkoxy) group, and then oxidizing the sulfur atom of the compound.

As the method for the oxidation, an ordinary method for converting sulfur atom into sulfinyl group or sulfonyl group can be applied, and for example, an oxidation reaction with aqueous hydrogen peroxide using a catalytic amount of sodium tungstate or molybdenum dioxide dichloride, or sodium periodate, potassium periodate, meta-chloroperbenzoic acid (mCPBA), PCC, PDC, N-chlorosuccinimide (NCS), N-bromosuccinimide (NBS), N-iodosuccinimide (NIS), iodine, bromine, and the like may be used. As the solvent, although not particularly limited, examples include, for example, water, acetonitrile, acetone, tetrahydrofuran, dichloromethane, chloroform, 1,2-dichloroethane, carbon tetrachloride, N,N-dimethylformamide, acetic acid, and the like.

The compound having a (lower alkyl)sulfonyl(lower alkoxy) group as $R^{11}$ can also be prepared from the compound having an alkylsulfinyl(lower alkoxy) group as $R^{11}$ obtained by the method described above by using the same oxidation reaction conditions.

Intermediate compounds and target compounds obtained by the aforementioned reactions can be isolated and purified as required by purification methods commonly used in the field of synthetic organic chemistry, for example, filtration, extraction, washing, drying, concentration, recrystallization, various types of chromatography, and the like. Intermediate compounds may also be used for successive reactions without particular purification.

The resulting compound (I) can be made into an acid addition salt by an ordinary method. The compound may also be obtained as a solvate with a solvent such as a reaction solvent and a recrystallization solvent or a hydrate.

Examples of dosage form of the medicament comprising the compound of the present invention, a salt thereof or a solvate thereof as an active ingredient include, for example, those for oral administration such as tablet, capsule, granule, powder and syrup, and those for parenteral administration such as intravenous injection, intramuscular injection, suppository, inhalant, transdermal preparation, eye drop and nasal drop. In order to prepare medicinal formulations in the various dosage forms, the active ingredient may be used alone, or may be used in appropriate combination with other pharmaceutically acceptable additives such as excipients, binders, fillers, disintegrating agents, surface active agents, lubricants, dispersing agents, buffering agents, preservatives, corrigents, perfumes, coating agents and diluents to obtain as a pharmaceutical composition.

The HMG-CoA reductase inhibitor used for the combinatory composition for the medicament of the present invention is a compound which inhibits the biological conversion of hydroxymethylglutaryl-coenzyme A into mevalonic acid, catalyzed by the HMG-CoA reductase, and examples include lovastatin, simvastatin, fluvastatin, pravastatin, pitavastatin, atorvastatin, rosvastatin and the like.

Although a dose of the medicament of the present invention may vary depending on the weight, age, sexuality, and symptoms of a patient and the like, it is generally preferred that 1 to 2000 mg, especially 10 to 300 mg, in terms of the compound represented by the general formula (I), may be orally or parenterally administered at one time or several times as divided portions per day for an adult.

EXAMPLES

The present invention will be explained with reference to examples. However, the present invention is not limited to these examples.

Example 1

Preparation of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine 5-Bromo-2-chloropyrimidine (300 mg, 1.55 mmol) was dissolved by heating at 120° C. in 4-methoxybenzylamine (2.1 g, 15.4 mmol), and the solution was stirred at the same temperature for 2 hours. The reaction mixture was directly subjected to silica gel column chromatography for purification to obtain 5-bromo-2-(4-methoxybenzylamino)pyrimidine (445 mg, 98%) as colorless amorphous solid.

$^1$H-NMR (CDCl$_3$) δ: 3.80 (3H, s), 4.52 (2H, d, J=5.4 Hz), 5.45 (1H, br), 6.87 (2H, d, J=8.4 Hz), 7.24 (2H, d, J=8.4 Hz), 8.28 (2H, s).

Colorless amorphous solid of 5-bromo-2-(4-methoxybenzylamino)pyrimidine (300 mg, 1.02 mmol) was suspended in toluene (20 mL), the suspension was added with cuprous iodide (200 mg, 1.05 mmol), 2-methylthioethanol (1.06 g, 11.5 mmol), N,N'-dimethyldiaminoethane (0.83 g, 9.42 mmol) and cesium carbonate (400 mg, 1.22 mmol), and the mixture was stirred at 110° C. for 66 hours in an argon atmosphere. The reaction mixture was separated by silica gel column chromatography, and then purified by preparative silica gel thin layer chromatography to obtain 2-(4-methoxybenzylamino)-5-(2-methylthioethoxy)pyrimidine as colorless amorphous solid (172 mg).

$^1$H-NMR (CDCl$_3$) δ: 2.20 (3H, s), 2.85 (2H, t, J=6.8 Hz), 3.80 (3H, s), 4.10 (2H, t, J=6.8 Hz), 4.51 (2H, d, J=5.9 Hz), 5.31 (1H, br), 6.86 (2H, d, J=8.6 Hz), 7.28 (2H, d, J=8.6 Hz), 8.05 (2H, s).

Colorless amorphous solid of 2-(4-methoxybenzylamino)-5-(2-methylthioethoxy)pyrimidine (172 mg) was dissolved in trifluoroacetic acid (3 mL) at room temperature, and the solution was stirred at 60° C. for 2.5 hours. The reaction mixture was concentrated under reduced pressure, and the resulting residue was purified by preparative silica gel thin layer chromatography to obtain 2-amino-5-(2-methylthioethoxy)pyrimidine (34 mg, 18% for 2 steps) as colorless amorphous solid.

$^1$H-NMR (CDCl$_3$) δ: 2.21 (3H, s), 2.85 (2H, t, J=6.6 Hz), 4.13 (2H, t, J=6.6 Hz), 4.93 (2H, br), 8.06 (2H, s).

A solution of 3-bromo-2-hydroxymethyl-6-methoxypyridine (10.6 g, 48.6 mmol) synthesized by the method described in Organic & Biomolecular Chemistry 1 (16) 2865-2876 (2003) in methylene chloride (150 mL) was successively added dropwise with diisopropylethylamine (31.4 g, 243 mmol) and chloromethyl methyl ether (13.3 g, 165 mmol) under ice cooling. The mixture was warmed to room temperature, stirred for 16 hours, and then added with methanol (30 mL), and the mixture was stirred for 30 minutes. The reaction mixture was concentrated under reduced pressure, and the resulting residue was purified by silica gel column chromatography (hexane:ethyl acetate=30:1→20:1) to obtain 3-bromo-6-methoxy-2-(methoxymethyloxy)methylpyridine (12.1 g, 95%) as pale yellow oil.

$^1$H-NMR (CDCl$_3$) δ: 3.46 (3H, s), 3.93 (3H, s), 4.73 (2H, s), 4.81 (2H, s), 6.59 (1H, d, J=8.7 Hz), 7.68 (1H, d, J=8.7 Hz).

A solution of 3-bromo-6-methoxy-2-(methoxymethyloxy)methylpyridine (1.5 g, 5.72 mmol), tris(dibenzylideneacetone)(chloroform)dipalladium(0) (592 mg, 0.572 mmol), (2-biphenyl)di-t-butylphosphine (680 mg, 2.28 mmol), sodium t-butoxide (1.65 g, 17.2 mmol) and ethylamine (2.0 mol/L solution in tetrahydrofuran, 15 mL, 30 mmol) in tetrahydrofuran (15 mL) was heated to 135° C. over 3 minutes under microwave irradiation (500 W). The reaction mixture was cooled, and then filtered through Celite, and washed with ethyl acetate. The reaction mixture was concentrated under reduced pressure, and the resulting residue was purified by silica gel column chromatography (hexane:ethyl acetate=8:1) to obtain 3-ethylamino-6-methoxy-2-(methoxymethyloxy)methylpyridine (954 mg, 74%) as yellow oil.

$^1$H-NMR (CDCl$_3$) δ: 1.27 (3H, t, J=7.1 Hz), 3.12 (2H, q, J=7.1 Hz), 3.43 (3H, s), 3.86 (3H, s), 4.23 (1H br s), 4.68 (2H, s), 4.71 (2H, s), 6.64 (1H, d, J=8.8 Hz), 7.03 (1H, d, J=8.8 Hz).

A solution of 3-ethylamino-6-methoxy-2-(methoxymethyloxy)methylpyridine (7.20 g, 31.8 mmol) and cyclopentanecarboaldehyde (3.75 g, 38.2 mmol) in 1,2-dichloroethane (240 mL) was added with sodium triacetoxyborohydride (8.75 g, 41.3 mmol), and the mixture was stirred at room temperature for 12 hours. The reaction mixture was added with water, and extracted with chloroform. The organic layers were combined, washed with water and saturated brine, dried over anhydrous sodium sulfate, and concentrated under reduced pressure. The resulting residue was purified by silica gel column chromatography (hexane:ethyl acetate=8:1) to obtain 3-(N-cyclopentylmethyl-N-ethyl)amino-6-methoxy-2-(methoxymethyloxy)methylpyridine (8.39 g, 86%) as pale yellow oil.

$^1$H-NMR (CDCl$_3$) δ: 0.94 (3H, t, J=7.1 Hz), 1.05-1.23 (2H, m), 1.34-1.70 (6H, m), 1.82 (1H, m), 2.78 (2H, d, J=7.5 Hz), 2.90 (2H, q, J=7.1 Hz), 3.47 (3H, s), 3.93 (3H, s), 4.76 (2H, s), 4.85 (2H, s), 6.67 (1H, d, J=8.8 Hz), 7.46 (1H, d, J=8.8 Hz).

A solution of 3-(N-cyclopentylmethyl-N-ethyl)amino-6-methoxy-2-(methoxymethyloxy)methylpyridine (8.39 g, 27.2 mmol) in a mixture of dioxane (400 mL) and water (100 mL) was added dropwise with concentrated hydrochloric acid (20 mL), and the mixture was stirred at 50° C. for 19 hours. The reaction mixture was made basic by adding aqueous sodium hydroxide, and extracted with ethyl acetate. The organic layers were combined, washed with water and saturated brine, dried over anhydrous sodium sulfate, and concentrated under reduced pressure. The resulting residue was purified by silica gel column chromatography (hexane:ethyl acetate=15:1) to obtain 3 (N-cyclopentylmethyl-N-ethyl)amino-2-hydroxymethyl-6-methoxypyridine (6.72 g, 94%) as pale yellow oil.

$^1$H-NMR (CDCl$_3$) δ: 0.96 (3H, t, J=7.1 Hz), 1.05-1.23 (2H, m), 1.33-1.77 (6H, m), 1.87 (1H, m), 2.77 (2H, d, J=7.5 Hz), 2.86 (2H, q, J=7.1 Hz), 3.94 (3H, s), 4.79 (2H, s), 5.04 (1H, br s), 6.64 (1H, d, J=8.7 Hz), 7.49 (1H, d, J=8.7 Hz).

A solution of 3-(N-cyclopentylmethyl-N-ethyl)amino-2-hydroxymethyl-6-methoxypyridine (2.0 g, 7.57 mmol) in chloroform (200 mL) was added with manganese dioxide (20 g, 230 mmol), and the mixture was stirred at 55° C. for 16 hours. The reaction mixture was filtered through Celite, and then the filtrate was washed with chloroform and concentrated under reduced pressure. The resulting residue was added with chloroform (200 mL) and manganese dioxide (20 g, 230 mmol), and the mixture was stirred at 55° C. for 6 hours. The reaction mixture was filtered through Celite, and washed with chloroform, and then the filtrate was concentrated under reduced pressure to obtain 2-[3-(N-cyclopentylmethyl-N-ethyl)amino-6-methoxypyridine]carboxyaldehyde (1.68 g, 85%) as pale yellow oil.

$^1$H-NMR (CDCl$_3$) δ: 1.02 (3H, t, J=7.1 Hz), 1.05-1.23 (2H, m), 1.36-1.73 (6H, m), 1.95 (1H, m), 2.99 (2H, d, J=7.6 Hz), 3.13 (2H, q, J=7.1 Hz), 3.99 (3H, s), 6.93 (1H, d, J=9.0 Hz), 7.59 (1H, d, J=9.0 Hz), 10.4 (1H, s).

A solution of 2-amino-5-(2-methylthioethoxy)pyrimidine (1.03 g, 5.55 mmol) and 2-[3-(N-cyclopentylmethyl-N-ethyl)amino-6-methoxypyridine]carboaldehyde (1.60 g, 6.10 mmol) in 1,2-dichloroethane (60 mL) was stirred at room temperature for 10 minutes, and then added with sodium triacetoxyborohydride (1.24 g, 5.83 mmol), and the mixture was stirred at room temperature for 12 hours. The reaction mixture was added with water, and extracted with chloroform. The organic layers were combined, washed with water and saturated brine, dried over anhydrous sodium sulfate, and concentrated under reduced pressure. The resulting residue was purified by silica gel column chromatography (hexane:ethyl acetate=5:1) to obtain 2-[N-[3-(N-cyclopentylmethyl-N-ethyl)amino-6-methoxypyridin-2-yl]methyl]amino-5-(2-methylthioethoxy)pyrimidine (1.60 g, 67%) as pale yellow oil.

$^1$H-NMR (CDCl$_3$) δ: 0.97 (3H, t, J=7.1 Hz), 1.08-1.25 (2H, m), 1.34-1.70 (6H, m), 1.84 (1H, m), 2.21 (3H, s), 2.81 (2H, d, J=7.5 Hz), 2.85 (2H, t, J=6.7 Hz), 2.91 (2H, q, J=7.1 Hz), 3.94 (3H, s), 4.12 (2H, t, J=6.7 Hz), 4.70 (2H, d, J=4.6 Hz), 6.33 (1H, t, J=4.6 Hz), 6.64 (1H, d, J=8.6 Hz), 7.47 (1H, d, J=8.6 Hz), 8.12 (2H, s).

A solution of 2-[N-[3-(N-cyclopentylmethyl-N-ethyl)amino-6-methoxypyridin-2-yl]methyl]amino-5-(2-methylthioethoxy)pyrimidine (45 mg, 0.10 mmol) in N,N-dimethylformamide (1.5 mL) was added with sodium hydride (50% in oil, 20 mg, 0.42 mmol) under ice cooling, and the mixture was stirred at 50° C. for 30 minutes in an argon atmosphere. The reaction mixture was cooled to −15° C., added dropwise with a solution of 3-trifluoromethylbenzyl bromide (50 mg, 0.21 mmol) in N,N-dimethylformamide (1.0 mL), and then the mixture was stirred at the same temperature for 15 minutes and at room temperature for 30 minutes. The reaction mixture was added with water, and extracted with ethyl acetate. The organic layers were combined, washed with water and saturated brine, dried over anhydrous sodium sulfate, and concentrated under reduced pressure. The resulting residue was purified by preparative silica gel thin layer chromatography (hexane:acetone=5:1) to obtain the title compound (35.5 mg, 58%) as pale yellow oil.

Example 2

Preparation of 2-[N-[3-(N-cyclopentylmethyl-N-ethyl)amino-6-methoxypyridin-2-yl]methyl-N-(3-trifluoromethylbenzyl)]amino-5-(2-methylsulfinylethoxy)pyrimidine A solution of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine (34.3 mg, 0.058 mmol) in acetic acid (1.5 mL) was added with sodium perborate (10.7 mg, 0.070 mmol), and the mixture was stirred at room temperature for 3 hours. The reaction mixture was added with aqueous sodium hydroxide, and extracted with ethyl acetate. The organic layers were combined, washed with water and saturated brine, dried over anhydrous sodium sulfate, and concentrated under reduced pressure. The resulting residue was purified by preparative silica gel thin layer chromatography (chloroform:methanol=20:1) to obtain the title compound (23.3 mg, 66%) as pale yellow oil.

Example 3

Preparation of 2-[N-[3-(N-cyclopentylmethyl-N-ethyl)amino-6-methoxypyridin-2-yl]methyl-N-(3-trifluoromethylbenzyl)]amino-5-(2-methylsulfonylethoxy)pyrimidine A solution of 2-[N-[3-(N-cyclopentylmethyl-N-ethyl)amino-6-methoxypyridin-2-yl]methyl-N-(3-trifluoromethylbenzyl)]amino-5-(2-methylsulfinylethoxy)pyrimidine (15.0 mg, 0.025 mmol) in acetonitrile (0.8 mL) was added dropwise with a solution of aqueous hydrogen peroxide (30%, 10.3 mg, 0.099 mmol) in acetonitrile (0.4 mL) and a solution of molybdenum dioxide dichloride (0.74 mg, 0.0037 mmol) in acetonitrile (0.4 mL), and the mixture was stirred at room temperature for 24 hours. The reaction mixture was added with water, and extracted with ethyl acetate. The organic layers were combined, washed with water and saturated brine, dried over anhydrous sodium sulfate, and concentrated under reduced pressure. The resulting residue was purified by preparative silica gel thin layer chromatography (chloroform:methanol=30:1) to obtain the title compound (8.4 mg, 55%) as pale yellow oil.

Example 4

Preparation of 2-[N-benzyl-N-[3-(N-cyclopentylmethyl-N-ethyl)amino-6-methoxypyridin-2-yl]methyl]amino-5-(2-methylthioethoxy)pyrimidine By using benzyl bromide instead of 3-trifluoromethylbenzyl bromide, reactions and treatments were performed in the same manner as those of Example 1 to obtain the title compound as pale yellow oil.

Example 5

Preparation of 2-[N-benzyl-N-[3-(N-cyclopentylmethyl-N-ethyl)amino-6-methoxypyridin-2-yl]methyl]amino-5-(2-methylsulfinylethoxy)pyrimidine By using 2-[N-benzyl-N-[3-(N-cyclopentylmethyl-N-ethyl)amino-6-methoxypyridin-2-yl]methyl]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as pale yellow oil.

Example 6

Preparation of 2-[N-benzyl-N-[3-(N-cyclopentylmethyl-N-ethyl)amino-6-methoxypyridin-2-yl]methyl]amino-5-(2-methylsulfonylethoxy)pyrimidine By using 2-[N-benzyl-N-[3-(N-cyclopentylmethyl-N-ethyl)amino-6-methoxypyridin-2-yl]methyl]amino-5-(2-methylsulfinylethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylsulfinylethoxy)pyrimidine, reactions and treatments were performed in the same manner as those of Example 3 to obtain the title compound as yellow oil.

Examples 7 and 8

Preparation of 2-[N-(3-cyano-5-trifluoromethylbenzyl)-N-[3-(N-cyclopentylmethyl-N-ethyl)amino-6-methoxypyridin-2-yl]methyl]amino-5-(2-methylthioethoxy)pyrimidine (compound of Example 7) and 2-[N-(3-cyano-5-trifluoromethylbenzyl)-N-[3-(N-cyclopentylmethyl-N-ethyl)amino-6-methoxypyridin-2-yl]methyl]amino-5-(3-cyano-5-trifluoromethylbenzyloxy)pyrimidine (compound of Example 8)

By using 3-cyano-5-trifluoromethylbenzyl bromide synthesized by the method described in Japanese Patent Unexamined Publication (Kokai) No. 2003-221376 instead of 3-trifluoromethylbenzyl bromide, reactions and treatments were performed in the same manner as those of Example 1 to obtain 2-[N-(3-cyano-5-trifluoromethylbenzyl)-N-[3-(N-cyclopentylmethyl-N-ethyl)amino-6-methoxypyridin-2-yl]methyl]amino-5-(2-methylthioethoxy)pyrimidine (compound of Example 7) as pale red oil. As a by-product, 2-[N-(3-cyano-5-trifluoromethylbenzyl)-N-[3-(N-cyclopentylmethyl-N-ethyl)amino-6-methoxypyridin-2-yl]methyl]amino-5-(3-cyano-5-trifluoromethylbenzyloxy)pyrimidine (compound of Example 8) was also obtained as yellow oil.

Example 9

Preparation of 2-[N-(3-cyano-5-trifluoromethylbenzyl)-N-[3-(N-cyclopentylmethyl-N-ethyl)amino-6-methoxypyridin-2-yl]methyl]amino-5-(2-methylsulfinylethoxy)pyrimidine By using 2-[N-(3-cyano-5-trifluoromethylbenzyl)-N-[3-(N-cyclopentylmethyl-N-ethyl)amino-6-methoxypyridin-2-yl]methyl]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as pale yellow oil.

Example 10

Preparation of 2-[N-(3-cyano-5-trifluoromethylbenzyl)-N-[3-(N-cyclopentylmethyl-N-ethyl)amino-6-methoxypyridin-2-yl]methyl]amino-5-(2-methylsulfonylethoxy)pyrimidine By using 2-[N-(3-cyano-5-trifluoromethylbenzyl)-N-[3-(N-cyclopentylmethyl-N-ethyl)amino-6-methoxypyridin-2-yl]methyl]amino-5-(2-methylsulfinylethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylsulfinylethoxy)pyrimidine, reactions and treatments were performed in the same manner as those of Example 3 to obtain yellow oil. This oil was crystallized from methanol to obtain the title compound as pale yellow crystalline powder.

Example 11

Preparation of 2-[N-[3,5-bis(trifluoromethyl)benzyl]-N-[3-(N-cyclopentylmethyl-N-ethyl)amino-6-methoxypyridin-2-yl]methyl]amino-5-(2-methylthioethoxy)pyrimidine By using 3,5-bis(trifluoromethyl)benzyl bromide instead of 3-trifluoromethylbenzyl bromide, reactions and treatments were performed in the same manner as those of Example 1 to obtain the title compound as yellow oil.

Example 12

Preparation of 2-[N-[3,5-bis(trifluoromethyl)benzyl]-N-[3-(N-cyclopentylmethyl-N-ethyl)amino-6-methoxypyridin-2-yl]methyl]amino-5-(2-methylsulfinylethoxy)pyrimidine By using 2-[N-[3,5-bis(trifluoromethyl)benzyl]-N-[3-(N-cyclopentylmethyl-N-ethyl)amino-6-methoxypyridin-2-yl]methyl]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as pale yellow oil.

Example 13

Preparation of 2-[N-[3,5-bis(trifluoromethyl)benzyl]-N-[3-(N-cyclopentylmethyl-N-ethyl)amino-6-methoxypyridin-2-yl]methyl]amino-5-(2-methylsulfonylethoxy)pyrimidine By using 2-[N-[3,5-bis(trifluoromethyl)benzyl]-N-[3-(N-cyclopentylmethyl-N-ethyl)amino-6-methoxypyridin-2-yl]methyl]amino-5-(2-methylsulfinylethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylsulfinylethoxy)pyrimidine, reactions and treatments were performed in the same manner as those of Example 3 to obtain the title compound as brown oil.

A solution of this brown oil (2.02 g, 2.93 mmol) in methanol (90 mL) was added dropwise with a solution of hydrochloric acid in methanol (10%, 9.8 mL) under ice cooling, and the reaction mixture was stirred at the same temperature for 5 minutes, and then concentrated under reduced pressure to obtain 2-[N-[3,5-bis(trifluoromethyl)benzyl]-N-[3-(N-cyclopentylmethyl-N-ethyl)amino-6-methoxypyridin-2-yl]methyl]amino-5-(2-methylsulfonylethoxy)pyrimidine trihydrochloride (2.30 g, 98%) as pale yellow crystalline powder.

Melting point: 67-71° C.

IR (ATR) cm$^{-1}$: 2950, 1614, 1541, 1482, 1430.

$^1$H-NMR (CD$_3$OD) δ: 0.99 (3H, t, J=7.0 Hz), 1.10-1.35 (2H, m), 1.40-1.80 (6H, m), 2.03 (1H, m), 3.09 (3H, s), 3.62 (2H, t, J=5.4 Hz), 3.75 (2H, d, J=7.3 Hz), 3.78-3.86 (5H, m), 4.51 (2H, t, J=5.4 Hz), 5.03 (2H, s), 5.26 (2H, s), 7.01 (1H, d, J=9.1 Hz), 7.86 (1H, s), 7.88 (2H, s), 8.09 (1H, d, J=9.1 Hz), 8.46 (2H, s).

Example 14

Preparation of 2-[N-(3-cyanobenzyl)-N-[3-(N-cyclopentylmethyl-N-ethyl)amino-6-methoxypyridin-2-yl]methyl]amino-5-(2-methylthioethoxy)pyrimidine By using 3-cyanobenzyl bromide instead of 3-trifluoromethylbenzyl bromide, reactions and treatments were performed in the same manner as those of Example 1 to obtain the title compound as pale yellow oil.

Example 15

Preparation of 2-[N-(3-cyanobenzyl)-N-[3-(N-cyclopentylmethyl-N-ethyl)amino-6-methoxypyridin-2-yl]methyl]amino-5-(2-methylsulfinylethoxy)pyrimidine By using 2-[N-(3-cyanobenzyl)-N-[3-(N-cyclopentylmethyl-N-ethyl)amino-6-methoxypyridin-2-yl]methyl]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as yellow oil.

Example 16

Preparation of 2-[N-[2,5-bis(trifluoromethyl)benzyl]-N-[3-(N-cyclopentylmethyl-N-ethyl)amino-6-methoxypyridin-2-yl]methyl]amino-5-(2-methylthioethoxy)pyrimidine By using 2,5-bis(trifluoromethyl)benzyl bromide instead of 3-trifluoromethylbenzyl bromide, reactions and treatments were performed in the same manner as those of Example 1 to obtain the title compound as pale yellow oil.

Example 17

Preparation of 2-[N-[2,5-bis(trifluoromethyl)benzyl]-N-[3-(N-cyclopentylmethyl-N-ethyl)amino-6-methoxypyridin-2-yl]methyl]amino-5-(2-methylsulfinylethoxy)pyrimidine By using 2-[N-[2,5-bis(trifluoromethyl)benzyl]-N-[3-(N-cyclopentylmethyl-N-ethyl)amino-6-methoxypyridin-2-yl]methyl]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as yellow oil.

Example 18

Preparation of 2-[N-[3-(N-cyclopentylmethyl-N-ethyl)amino-6-methoxypyridin-2-yl]methyl-N-(3,5-difluorobenzyl)]amino-5-(2-methylthioethoxy)pyrimidine By using 3,5-difluorobenzyl bromide instead of 3-trifluoromethylbenzyl bromide, reactions and treatments were performed in the same manner as those of Example 1 to obtain the title compound as yellow oil.

Example 19

Preparation of 2-[N-[3-(N-cyclopentylmethyl-N-ethyl)amino-6-methoxypyridin-2-yl]methyl-N-(3,5-difluorobenzyl)]amino-5-(2-methylsulfinylethoxy)pyrimidine By using 2-[N-[3-(N-cyclopentylmethyl-N-ethyl)amino-6-methoxypyridin-2-yl]methyl-N-(3,5-difluorobenzyl)]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as pale yellow oil.

Example 20

Preparation of 2-[N-[3-(N-cyclopentylmethyl-N-ethyl)amino-6-methoxypyridin-2-yl]methyl-N-(3,5-difluorobenzyl)]amino-5-(2-methylsulfonylethoxy)pyrimidine By using 2-[N-[3-(N-cyclopentylmethyl-N-ethyl)amino-6-methoxypyridin-2-yl]methyl-N-(3,5-difluorobenzyl)]amino-5-(2-methylsulfinylethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylsulfinylethoxy)pyrimidine, reactions and treatments were performed in the same manner as those of Example 3 to obtain the title compound as reddish brown oil.

Example 21

Preparation of 2-[N-[3-(N-cyclopentylmethyl-N-ethyl)amino-6-methoxypyridin-2-yl]methyl-N-(3,5-dichlorobenzyl)]amino-5-(2-methylthioethoxy)pyrimidine By using 3,5-dichlorobenzyl bromide instead of 3-trifluoromethylbenzyl bromide, reactions and treatments were performed in the same manner as those of Example 1 to obtain the title compound as pale yellow oil.

Example 22

Preparation of 2-[N-[3-(N-cyclopentylmethyl-N-ethyl)amino-6-methoxypyridin-2-yl]methyl-N-(3,5-dichlorobenzyl)]amino-5-(2-methylsulfinylethoxy)pyrimidine By using 2-[N-[3-(N-cyclopentylmethyl-N-ethyl)amino-6-methoxypyridin-2-yl]methyl-N-(3,5-dichlorobenzyl)]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as pale yellow oil.

Example 23

Preparation of 2-[N-[3-(N-cyclopentylmethyl-N-ethyl)amino-6-methoxypyridin-2-yl]methyl-N-(3,5-dimethoxybenzyl)]amino-5-(2-methylthioethoxy)pyrimidine By using 3,5-dimethoxybenzyl bromide instead of 3-trifluoromethylbenzyl bromide, reactions and treatments were performed in the same manner as those of Example 1 to obtain the title compound as pale yellow oil.

Example 24

Preparation of 2-[N-[3-(N-cyclopentylmethyl-N-ethyl)amino-6-methoxypyridin-2-yl]methyl-N-(3,5-dimethoxybenzyl)]amino-5-(2-methylsulfinylethoxy)pyrimidine By using 2-[N-[3-(N-cyclopentylmethyl-N-ethyl)amino-6-methoxypyridin-2-yl]methyl-N-(3,5-dimethoxybenzyl)]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as pale yellow oil.

Example 25

Preparation of 2-[N-[3-(N-cyclopentylmethyl-N-ethyl)amino-6-methoxypyridin-2-yl]methyl-N-(3,5-dimethoxybenzyl)]amino-5-(2-methylsulfonylethoxy)pyrimidine By using 2-[N-[3-(N-cyclopentylmethyl-N-ethyl)amino-6-methoxypyridin-2-yl]methyl-N-(3,5-dimethoxybenzyl)]amino-5-(2-methylsulfinylethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylsulfinylethoxy)pyrimidine, reactions and treatments were performed in the same manner as those of Example 3 to obtain the title compound as pale yellow oil.

Example 26

Preparation of 2-[N-[3-(N-cyclopentylmethyl-N-ethyl)amino-6-methoxypyridin-2-yl]methyl-N-(3-trifluoromethoxybenzyl)]amino-5-(2-methylthioethoxy)pyrimidine By using 3-trifluoromethoxybenzyl bromide instead of 3-trifluoromethylbenzyl bromide, reactions and treatments were performed in the same manner as those of Example 1 to obtain the title compound as yellow oil.

Example 27

Preparation of 2-[N-[3-(N-cyclopentylmethyl-N-ethyl)amino-6-methoxypyridin-2-yl]methyl-N-(3-trifluoromethoxybenzyl)]amino-5-(2-methylsulfinylethoxy)pyrimidine By using 2-[N-[3-(N-cyclopentylmethyl-N-ethyl)amino-6-methoxypyridin-2-yl]methyl-N-(3-trifluoromethoxybenzyl)]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as yellow oil.

Example 28

Preparation of 2-[N-[3-(N-cyclopentylmethyl-N-ethyl)amino-6-methoxypyridin-2-yl]methyl-N-(3-trifluoromethoxybenzyl)]amino-5-(2-methylsulfonylethoxy)pyrimidine By using 2-[N-[3-(N-cyclopentylmethyl-N-ethyl)amino-6-methoxypyridin-2-yl]methyl-N-(3-trifluoromethoxybenzyl)]amino-5-(2-methylsulfinylethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylsulfinylethoxy)pyrimidine, reactions and treatments were performed in the same manner as those of Example 3 to obtain the title compound as reddish brown oil.

Example 29

Preparation of 2-[N-[3-(N-cyclopentylmethyl-N-ethyl)amino-6-methoxypyridin-2-yl]methyl-N-(3,5-dimethylbenzyl)]amino-5-(2-methylthioethoxy)pyrimidine By using 3,5-dimethylbenzyl bromide instead of 3-trifluoromethylbenzyl bromide, reactions and treatments were performed in the same manner as those of Example 1 to obtain the title compound as pale yellow oil.

Example 30

Preparation of 2-[N-[3-(N-cyclopentylmethyl-N-ethyl)amino-6-methoxypyridin-2-yl]methyl-N-(3,5-dimethylbenzyl)]amino-5-(2-methylsulfinylethoxy)pyrimidine By using 2-[N-[3-(N-cyclopentylmethyl-N-ethyl)amino-6-methoxypyridin-2-yl]methyl-N-(3,5-dimethylbenzyl)]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as pale yellow oil.

Example 31

Preparation of 2-[N-[3-(N-cyclopentylmethyl-N-ethyl)amino-6-methoxypyridin-2-yl]methyl-N-(3,4-difluorobenzyl)]amino-5-(2-methylthioethoxy)pyrimidine By using 3,4-difluorobenzyl bromide instead of 3-trifluoromethylbenzyl bromide, reactions and treatments were performed in the same manner as those of Example 1 to obtain the title compound as pale yellow oil.

Example 32

Preparation of 2-[N-[3-(N-cyclopentylmethyl-N-ethyl)amino-6-methoxypyridin-2-yl]methyl-N-(3,4-difluorobenzyl)]amino-5-(2-methylsulfinylethoxy)pyrimidine By using 2-[N-[3-(N-cyclopentylmethyl-N-ethyl)amino-6-methoxypyridin-2-yl]methyl-N-(3,4-difluorobenzyl)]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as pale yellow oil.

Example 33

Preparation of 2-[N-[3-(N-cyclopentylmethyl-N-ethyl)amino-6-methoxypyridin-2-yl]methyl-N-(2,5-difluorobenzyl)]amino-5-(2-methylthioethoxy)pyrimidine By using 2,5-difluorobenzyl bromide instead of 3-trifluoromethylbenzyl bromide, reactions and treatments were performed in the same manner as those of Example 1 to obtain the title compound as pale yellow oil.

Example 34

Preparation of 2-[N-[3-(N-cyclopentylmethyl-N-ethyl)amino-6-methoxypyridin-2-yl]methyl-N-(2,5-difluorobenzyl)]amino-5-(2-methylsulfinylethoxy)pyrimidine By using 2-[N-[3-(N-cyclopentylmethyl-N-ethyl)amino-6-methoxypyridin-2-yl]methyl-N-(2,5-difluorobenzyl)]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as pale yellow oil.

Example 35

Preparation of 2-[N-[3-(N-cyclopentylmethyl-N-ethyl)amino-6-methoxypyridin-2-yl]methyl-N-(2,6-difluorobenzyl)]amino-5-(2-methylthioethoxy)pyrimidine By using 2,6-difluorobenzyl bromide instead of 3-trifluoromethylbenzyl bromide, reactions and treatments were performed in the same manner as those of Example 1 to obtain the title compound as pale yellow oil.

Example 36

Preparation of 2-[N-[3-(N-cyclopentylmethyl-N-ethyl)amino-6-methoxypyridin-2-yl]methyl-N-(2,6-difluorobenzyl)]amino-5-(2-methylsulfinylethoxy)pyrimidine By using 2-[N-[3-(N-cyclopentylmethyl-N-ethyl)amino-6-methoxypyridin-2-yl]methyl-N-(2,6-difluorobenzyl)]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as pale yellow oil.

Examples 37 and 38

Preparation of 2-[N-[3-(N-cyclopentylmethyl-N-ethyl)amino-6-methoxypyridin-2-yl]methyl-N-(2,3-difluorobenzyl)]amino-5-(2-methylthioethoxy)pyrimidine (compound of Example 37) and 2-[N-[3-(N-cyclopentylmethyl-N-ethyl)amino-6-methoxypyridin-2-yl]methyl-N-(2,3-difluorobenzyl)]amino-5-(2,3-difluorobenzyloxy)pyrimidine (compound of Example 38)

By using 2,3-difluorobenzyl bromide instead of 3-trifluoromethylbenzyl bromide, reactions and treatments were performed in the same manner as those of Example 1 to obtain 2-[N-[3-(N-cyclopentylmethyl-N-ethyl)amino-6-methoxypyridin-2-yl]methyl-N-(2,3-difluorobenzyl)]amino-5-(2-methylthioethoxy)pyrimidine (compound of Example 37) as pale yellow oil. As a by-product, 2-[N-[3-(N-cyclopentylmethyl-N-ethyl)amino-6-methoxypyridin-2-yl]methyl-N-(2,3-difluorobenzyl)]amino-5-(2,3-difluorobenzyloxy)pyrimidine (compound of Example 38) was also obtained as pale yellow oil.

Example 39

Preparation of 2-[N-[3-(N-cyclopentylmethyl-N-ethyl)amino-6-methoxypyridin-2-yl]methyl-N-(2,3-difluorobenzyl)]amino-5-(2-methylsulfinylethoxy)pyrimidine By using 2-[N-[3-(N-cyclopentylmethyl-N-ethyl)amino-6-methoxypyridin-2-yl]methyl-N-(2,3-difluorobenzyl)]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as pale yellow oil.

Example 40

Preparation of 2-[N-[3-(N-cyclopentylmethyl-N-ethyl)amino-6-methoxypyridin-2-yl]methyl-N-(3,5-dicyanobenzyl)]amino-5-(2-methylthioethoxy)pyrimidine By using 3,5-dicyanobenzyl bromide synthesized by the method described in Journal of Organic Chemistry 55(3) 1040-1043 (1990) instead of 3-trifluoromethylbenzyl bromide, reactions and treatments were performed in the same manner as those of Example 1 to obtain the title compound as pale yellow oil.

Example 41

Preparation of 2-[N-[3-(N-cyclopentylmethyl-N-ethyl)amino-6-methoxypyridin-2-yl]methyl-N-(3,5-dicyanobenzyl)]amino-5-(2-methylsulfinylethoxy)pyrimidine By using 2-[N-[3-(N-cyclopentylmethyl-N-ethyl)amino-6-methoxypyridin-2-yl]methyl-N-(3,5-dicyanobenzyl)]

amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as pale yellow oil.

Example 42

Preparation of 2-[N-[3-(N-cyclopentylmethyl-N-ethyl)amino-6-methoxypyridin-2-yl]methyl-N-(3,5-dicyanobenzyl)]amino-5-(2-methylsulfonylethoxy)pyrimidine By using 2-[N-[3-(N-cyclopentylmethyl-N-ethyl)amino-6-methoxypyridin-2-yl]methyl-N-(3,5-dicyanobenzyl)]amino-5-(2-methylsulfinylethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylsulfinylethoxy)pyrimidine, reactions and treatments were performed in the same manner as those of Example 3 to obtain the title compound as yellow oil.

Example 43

Preparation of 2-[N-[3-(N-cyclopentylmethyl-N-ethyl)amino-6-methoxypyridin-2-yl]methyl-N-(4-trifluoromethylbenzyl)]amino-5-(2-methylthioethoxy)pyrimidine By using 4-trifluoromethylbenzyl bromide instead of 3-trifluoromethylbenzyl bromide, reactions and treatments were performed in the same manner as those of Example 1 to obtain the title compound as yellow oil.

Example 44

Preparation of 2-[N-[3-(N-cyclopentylmethyl-N-ethyl)amino-6-methoxypyridin-2-yl]methyl-N-(4-trifluoromethylbenzyl)]amino-5-(2-methylsulfinylethoxy)pyrimidine By using 2-[N-[3-(N-cyclopentylmethyl-N-ethyl)amino-6-methoxypyridin-2-yl]methyl-N-(4-trifluoromethylbenzyl)]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as yellow oil.

Example 45

Preparation of 2-[N-[3-(N-cyclopentylmethyl-N-ethyl)amino-6-methoxypyridin-2-yl]methyl-N-(4-trifluoromethylbenzyl)]amino-5-(2-methylsulfonylethoxy)pyrimidine By using 2-[N-[3-(N-cyclopentylmethyl-N-ethyl)amino-6-methoxypyridin-2-yl]methyl-N-(4-trifluoromethylbenzyl)]amino-5-(2-methylsulfinylethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylsulfinylethoxy)pyrimidine, reactions and treatments were performed in the same manner as those of Example 3 to obtain the title compound as yellow oil.

Example 46

Preparation of 2-[N-[3,5-bis(trifluoromethyl)benzyl]-N-[3-(N-cyclopentylmethyl-N-ethyl)amino-6-methoxypyridin-2-yl]methyl]amino-5-bromopyrimidine By using 2-amino-5-bromopyrimidine instead of 2-amino-5-(2-methylthioethoxy)pyrimidine, reactions and treatments were performed in the same manner as those of Example 1 to obtain the title compound as colorless oil.

Example 47

Preparation of 2-[N-[3,5-bis(trifluoromethyl)benzyl]-N-[3-(N-cyclopentylmethyl-N-ethyl)amino-6-methoxypyridin-2-yl]methyl]amino-5-(4-morpholino)pyrimidine 2-Amino-5-bromopyrimidine (210 mg, 1.21 mmol) was suspended in toluene (10 mL), the suspension was added with sodium t-butoxide (200 mg, 2.08 mmol), morpholine (2.99 g, 34.3 mmol), tris(dibenzylideneacetone)dipalladium(0) (31.2 mg, 0.03 mmol) and (2-biphenyl)di-t-butylphosphine (36.0 mg, 0.12 mmol), and the mixture was stirred at 110° C. for 66 hours in an argon atmosphere. The reaction mixture was directly separated by silica gel column chromatography, and then purified by preparative silica gel thin layer chromatography to obtain 2-amino-5-(4-morpholino)pyrimidine as pale yellow solid (43.6 mg, 20%).

$^1$H-NMR (CDCl$_3$) δ: 3.02 (4H, t, J=4.6 Hz), 3.86 (4H, t, J=4.6 Hz), 4.80 (2H, br), 8.06 (2H, s).

By using 2-amino-5-(4-morpholino)pyrimidine instead of 2-amino-5-(2-methylthioethoxy)pyrimidine, reactions and treatments were performed in the same manner as those of Example 1 to obtain the title compound as pale yellow oil.

Example 48

Preparation of 2-[N-[3,5-bis(trifluoromethyl)benzyl]-N-[3-(N-cyclopentylmethyl-N-ethyl)amino-6-methoxypyridin-2-yl]methyl]amino-5-(piperidin-1-yl)pyrimidine By using piperidine instead of morpholine, reactions and treatments were performed in the same manner as those of Example 47 to obtain 2-amino-5-(piperidin-1-yl)pyrimidine.

$^1$H-NMR (CD$_3$OD) δ: 1.50-1.60 (2H, m), 1.65-1.77 (4H, m), 2.97 (4H, t, J=5.4 Hz), 8.06 (2H, s).

By using 2-amino-5-(piperidin-1-yl)pyrimidine instead of 2-amino-5-(2-methylthioethoxy)pyrimidine, reactions and treatments were performed in the same manner as those of Example 1 to obtain the title compound as brown oil.

Example 49

Preparation of 2-[N-[3,5-bis(trifluoromethyl)benzyl]-N-[6-methoxy-3-(pyrrolidin-1-yl)pyridin-2-yl]methyl]amino-5-(2-methylthioethoxy)pyrimidine A solution of 3-bromo-6-methoxy-2-(methoxymethyloxy)methylpyridine (324.6 mg, 1.24 mmol), tris(dibenzylideneacetone)(chloroform)dipalladium(0) (32.7 mg, 0.03 mmol), (2-biphenyl)di-t-butylphosphine (18.5 mg, 0.06 mmol), sodium t-butoxide (357 mg, 3.71 mmol) and pyrrolidine (640 mg, 3.74 mmol) in toluene (4.5 mL) was stirred at 135° C. for 3 hours in a sealed tube. The reaction mixture was extracted with chloroform/water, and the organic layer was washed with saturated brine, then dried over anhydrous sodium sulfate, and concentrated under reduced pressure. The resulting residue was purified by preparative silica gel thin layer chromatography (hexane:ethyl acetate=3:1) to obtain 6-methoxy-2-(methoxymethyloxy)methyl-3-(pyrrolidin-1-yl)pyridine (42.7 mg, 14%) as yellow oil.

$^1$H-NMR (CDCl$_3$): 1.88-1.98 (4H, m), 3.08-3.14 (4H, m), 3.46 (3H, s), 3.90 (3H, s), 4.70 (2H, s), 4.83 (2H, s), 6.63 (1H, d, J=8.8 Hz), 7.30 (1H, d, J=8.8 Hz).

By using 6-methoxy-2-(methoxymethyl)oxymethyl-3-(pyrrolidin-1-yl)pyridine instead of 3-(N-cyclopentylmethyl-N-ethyl)amino-6-methoxy-2-(methoxymethyloxy)methylpyridine and 3,5-bis(trifluoromethyl)benzyl bromide instead of 3-trifluoromethylbenzyl bromide, reactions and treatments were performed in the same manner as those of Example 1 to obtain the title compound as pale yellow oil.

Example 50

Preparation of 2-[N-[3,5-bis(trifluoromethyl)benzyl]-N-[6-methoxy-3-(pyrrolidin-1-yl)pyridin-2-yl]methyl]amino-5-(2-methylsulfinylethoxy)pyrimidine By using 2-[N-[3,5-bis(trifluoromethyl)benzyl]-N-[6-methoxy-3-(pyrrolidin-1-yl)pyridin-2-yl]methyl]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as yellow oil.

Example 51

Preparation of 2-[N-[3,5-bis(trifluoromethyl)benzyl]-N-[6-methoxy-3-(pyrrolidin-1-yl)pyridin-2-yl]methyl]amino-5-(2-methylsulfonylethoxy)pyrimidine By using 2-[N-[3,5-bis(trifluoromethyl)benzyl]-N-[6-methoxy-3-(pyrrolidin-1-yl)pyridin-2-yl]methyl]amino-5-(2-methylsulfinylethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylsulfinylethoxy)pyrimidine, reactions and treatments were performed in the same manner as those of Example 3 to obtain the title compound as yellow oil.

Example 52

Preparation of 2-[N-[3,5-bis(trifluoromethyl)benzyl]-N-[3-(cyclopentylmethyl)ethylamino-6-hydroxypyridin-2-yl]methyl]amino-5-(2-methylsulfonylethoxy)pyrimidine A solution of 2-[N-[3,5-bis(trifluoromethyl)benzyl]-N-[3-(N-cyclopentylmethyl-N-ethyl)amino-6-methoxypyridin-2-yl]methyl]amino-5-(2-methylsulfonylethoxy)pyrimidine trihydrochloride (20 mg, 0.025 mmol) in 1,2-dichloroethane (1.0 mL) was added dropwise with a solution of boron tribromide (1.0 mol/L in dichloromethane, 75 µL, 0.075 mmol) under ice cooling, and the mixture was stirred at room temperature for 1 hour and at 50° C. for 3 hours. The reaction mixture was cooled to room temperature, further added with boron tribromide (1.0 mol/L solution in dichloromethane, 450 µL, 0.45 mmol), and the mixture was stirred at 50° C. for 12 hours. The reaction mixture was added with water, and extracted with chloroform. The organic layers were combined, washed with water and saturated brine, dried over anhydrous sodium sulfate, and concentrated under reduced pressure. The resulting residue was purified by preparative silica gel thin layer chromatography (chloroform:methanol=20:1) to obtain the title compound (3.1 mg, 18%) as green oil.

Example 53

Preparation of 2-[N-(4-cyanobenzyl)-N-[3-(N-cyclopentylmethyl-N-ethyl)amino-6-methoxypyridin-2-yl]methyl]amino-5-(2-methylthioethoxy)pyrimidine By using 4-cyanobenzyl bromide instead of 3-trifluoromethylbenzyl bromide, reactions and treatments were performed in the same manner as those of Example 1 to obtain the title compound as yellow oil.

Example 54

Preparation of 2-[N—[N-(4-cyanobenzyl)-3-(N-cyclopentylmethyl-N-ethyl)amino-6-methoxypyridin-2-yl]methyl]amino-5-(2-methylsulfinylethoxy)pyrimidine By using 2-[N-(4-cyanobenzyl)-N-[3-(N-cyclopentylmethyl-N-ethyl)amino-6-methoxypyridin-2-yl]methyl]amino-5-(2-methylthioethoxy)pyrimidine instead of 2-[N-[3-(N-cyclopentylmethyl-N-ethyl)amino-6-methoxypyridin-2-yl]methyl-N-(3-trifluoromethylbenzyl)]amino-5-(2-methylthioethoxy)pyrimidine, reactions and treatments were performed in the same manner as those of Example 2 to obtain the title compound as pale yellow oil.

Example 55

Preparation of 2-[N-[3,5-bis(trifluoromethyl)benzyl]-N-[3-[N-ethyl-N-(4-methoxybenzyl)]amino-6-methoxypyridin-2-yl]methyl]amino-5-(2-methylthioethoxy)pyrimidine By using anisaldehyde instead of cyclopentanecarboaldehyde, reactions and treatments were performed in the same manner as those of Example 1 to obtain 2-[N-[3-[N-ethyl-N-(4-methoxybenzyl)]amino-6-methoxypyridin-2-yl]methyl]amino-5-(2-methylthioethoxy)pyrimidine as pale yellow oil.

$^1$H-NMR (CDCl$_3$) δ: 0.94 (3H, t, J=7.1 Hz), 2.21 (3H, s), 2.86 (2H, t, J=6.6 Hz), 2.92 (2H, q, J=7.1 Hz), 3.77 (3H, s), 3.93 (3H, s), 3.95 (2H, s), 4.12 (3H, t, J=6.6 Hz), 4.72 (2H, d, J=4.6 Hz), 6.30 (1H, t, J=4.6 Hz), 6.61 (1H, d, J=8.6 Hz), 6.80 (2H, d, J=8.6 Hz), 7.19 (2H, d, J=8.6 Hz), 7.38 (1H, d, J=8.6 Hz), 8.13 (2H, s).

By using 2-[N-[3-[N-ethyl-N-(4-methoxybenzyl)]amino-6-methoxypyridin-2-yl]methyl]amino-5-(2-methylthioethoxy)pyrimidine instead of 2-[N-[3-(N-cyclopentylmethyl-N-ethyl)amino-6-methoxypyridin-2-yl]methyl]amino-5-(2-methylthioethoxy)pyrimidine and 3,5-bis(trifluoromethyl)benzyl bromide instead of 3-trifluoromethylbenzyl bromide, reactions and treatments were performed in the same manner as those of Example 1 to obtain the title compound as yellow oil.

The compounds obtained in the aforementioned examples are shown in Table 1.

TABLE 1
| Example | Chemical formula | Physicochemical properties |
|---|---|---|
| 1 | 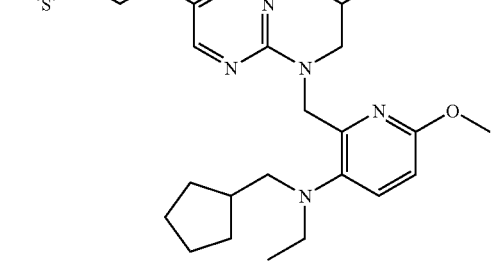 | ¹H-NMR (CDCl₃) δ: 0.91 (3 H, t, J = 7.1 Hz), 1.02-1.18 (2 H, m), 1.33-1.69 (6 H, m), 1.84 (1 H, m), 2.19 (3 H, s), 2.74 (2 H, d, J = 7.5 Hz), 2.78-2.90 (4 H, m), 3.57 (3 H, s), 4.11 (2 H, t, J = 6.7 Hz), 4.94 (2 H, s), 5.01 (2 H, s), 6.56 (1 H, d, J = 8.6 Hz), 7.33-7.60 (5 H, m), 8.09 (2 H, s). |
| 2 | 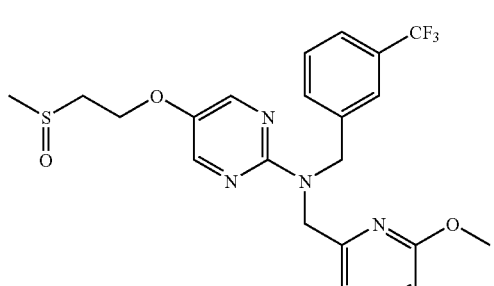 | ¹H-NMR (CDCl₃) δ: 0.91 (3 H, t, J = 7.1 Hz), 1.02-1.18 (2 H, m), 1.35-1.70 (6 H, m), 1.85 (1 H, m), 2.70 (3 H, s), 2.74 (2 H, d, J = 7.5 Hz), 2.84 (2 H, q, J = 7.1 Hz), 3.01 (1 H, m), 3.15 (1 H, m), 3.58 (3 H, s), 4.30-4.44 (2 H, m), 4.95 (2 H, s), 5.01 (2 H, s), 6.56 (1 H, d, J = 8.5 Hz), 7.32-7.55 (5 H, m), 8.11 (2 H, s). |
| 3 | 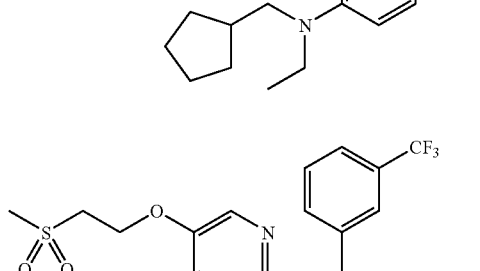 | ¹H-NMR (CDCl₃) δ: 0.92 (3 H, t, J = 7.1 Hz), 1.04-1.16 (2 H, m), 1.35-1.66 (6 H, m), 1.85 (1 H, m), 2.74 (2 H, d, J = 7.5 Hz), 2.85 (2 H, q, J = 7.1 Hz), 3.06 (3 H, s), 3.41 (2 H, t, J = 5.3 Hz), 3.59 (3 H, s), 4.38 (2 H, t, J = 5.3 Hz), 4.96 (2 H, s), 5.01 (2 H, s), 6.56 (1 H, d, J = 8.6 Hz), 7.32-7.54 (5 H, m), 8.10 (2 H, s). |
| 4 | 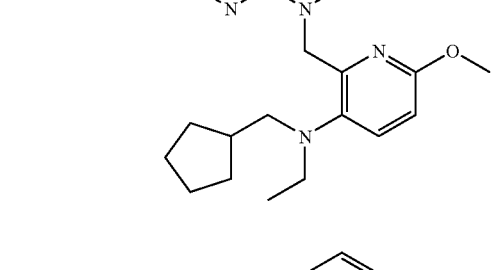 | ¹H-NMR (CDCl₃) δ: 0.91 (3 H, t, J = 7.1 Hz), 1.02-1.16 (2 H, m), 1.35-1.65 (6 H, m), 1.85 (1 H, m), 2.19 (3 H, s), 2.74 (2 H, d, J = 7.4 Hz), 2.76-2.87 (4 H, m), 3.59 (3 H, s), 4.09 (2 H, t, J = 6.8 Hz), 4.91 (2 H, s), 4.99 (2 H, s), 6.55 (1 H, d, J = 8.6 Hz), 7.16-7.32 (5 H, m), 7.39 (1 H, d, J = 8.6 Hz), 8.08 (2 H, s). |

TABLE 1-continued

| Example | Chemical formula | Physicochemical properties |
| --- | --- | --- |
| 5 | | ¹H-NMR (CDCl₃) δ: 0.91 (3 H, t, J = 7.1 Hz), 1.04-1.16 (2 H, m), 1.35-1.70 (6 H, m), 1.85 (1 H, m), 2.69 (3 H, s), 2.74 (2 H, d, J = 7.5 Hz), 2.84 (2 H, q, J = 7.1 Hz), 3.00 (1 H, m), 3.15 (1 H, m), 3.60 (3 H, s), 4.26-4.44 (2 H, m), 4.92 (2 H, s), 4.98 (2 H, s), 6.55 (1 H, d, J = 8.5 Hz), 7.18-7.32 (5 H, m), 7.40 (1 H, d, J = 8.5 Hz), 8.09 (2 H, s). |
| 6 | | ¹H-NMR (CDCl₃) δ: 0.92 (3 H, t, J = 7.0 Hz), 1.03-1.17 (2 H, m), 1.35-1.70 (6 H, m), 1.85 (1 H, m), 2.74 (2 H, d, J = 7.5 Hz), 2.84 (2 H, q, J = 7.0 Hz), 3.06 (3 H, s), 3.40 (2 H, t, J = 5.4 Hz), 3.61 (3 H, s), 4.37 (2 H, t, J = 5.4 Hz), 4.93 (2 H, s), 4.98 (2 H, s), 6.56 (1 H, d, J = 8.8 Hz), 7.15-7.35 (5 H, m), 7.41 (1 H, d, J = 8.8 Hz), 8.08 (2 H, s). |
| 7 | | ¹H-NMR (CDCl₃) δ: 0.94 (3 H, t, J = 7.0 Hz), 1.06-1.22 (2 H, m), 1.35-1.70 (6 H, m), 1.87 (1 H, m), 2.20 (3 H, s), 2.77 (2 H, d, J = 7.4 Hz), 2.80-2.92 (4 H, m), 3.55 (3 H, s), 4.12 (2 H, t, J = 6.6 Hz), 4.94 (2 H, s), 5.05 (2 H, s), 6.56 (1 H, d, J = 8.7 Hz), 7.41 (1 H, d, J = 8.7 Hz), 7.76 (2 H, s), 7.80 (1 H, s), 8.09 (2 H, s). |
| 8 | | ¹H-NMR (CDCl₃) δ: 0.95 (3 H, t, J = 7.1 Hz), 1.05-1.25 (2 H, m), 1.35-1.70 (6 H, m), 1.88 (1 H, m), 2.78 (2 H, d, J = 7.3 Hz), 2.88 (2 H, q, J = 7.1 Hz), 3.55 (3 H, s), 4.96 (2 H, s), 5.06 (2 H, s), 5.10 (2 H, s), 6.58 (1 H, d, J = 8.7 Hz), 7.42 (1 H, d, J = 8.7 Hz), 7.77 (2 H, s), 7.80 (1 H, s), 7.84-7.95 (3 H, m), 8.13 (2 H, s). |

TABLE 1-continued

| Example | Chemical formula | Physicochemical properties |
| --- | --- | --- |
| 9 | | $^1$H-NMR (CDCl$_3$) δ: 0.94 (3 H, t, J = 7.1 Hz), 1.06-1.20 (2 H, m), 1.35-1.65 (6 H, m), 1.87 (1 H, m), 2.70 (3 H, s), 2.77 (2 H, d, J = 7.5 Hz), 2.88 (2 H, q, J = 7.1 Hz), 3.03 (1 H, m), 3.16 (1 H, m), 3.56 (3 H, s), 4.30-4.46 (2 H, m), 4.95 (2 H, s), 5.05 (2 H, s), 6.57 (1 H, d, J = 8.9 Hz), 7.41 (1 H, d, J = 8.9 Hz), 7.76 (2 H, s), 7.79 (1 H, s), 8.11 (2 H, s). |
| 10 | | Melting point: 97.2-98.2° C.<br>IR (ATR)cm$^{-1}$: 2949, 2867, 1607, 1552, 1500, 1473.<br>$^1$H-NMR (CDCl$_3$) δ: 0.95 (3 H, t, J = 7.1 Hz), 1.06-1.20 (2 H, m), 1.37-1.67 (6 H, m), 1.87 (1 H, m), 2.77 (2 H, d, J = 7.6 Hz), 2.88 (2 H, q, J = 7.1 Hz), 3.07 (3 H, s), 3.43 (2 H, t, J = 5.3 Hz), 3.56 (3 H, s), 4.40 (2 H, t, J = 5.3 Hz), 4.95 (2 H, s), 5.05 (2 H, s), 6.58 (1 H, d, J = 8.8 Hz), 7.42 (1 H, d, J = 8.8 Hz), 7.76 (2 H, s), 7.79 (1 H, s), 8.10 (2 H, s). |
| 11 | | $^1$H-NMR (CDCl$_3$) δ: 0.92 (3 H, t, J = 7.0 Hz), 1.05-1.20 (2 H, m), 1.35-1.65 (6 H, m), 1.86 (1 H, m), 2.20 (3 H, s), 2.75 (2 H, d, J = 7.6 Hz), 2.79-2.90 (4 H, m), 3.54 (3 H, s), 4.11 (2 H, t, J = 6.8 Hz), 4.98 (2 H, s), 5.04 (2 H, s), 6.56 (1 H, d, J = 8.7 Hz), 7.40 (1 H, d, J = 8.7 Hz), 7.67-7.76 (3 H, m), 8.09 (2 H, s). |
| 12 | | $^1$H-NMR (CDCl$_3$) δ: 0.92 (3 H, t, J = 7.1 Hz), 1.05-1.19 (2 H, m), 1.35-1.70 (6 H, m), 1.86 (1 H, m), 2.70 (3 H, s), 2.75 (2 H, d, J = 7.6 Hz), 2.86 (2 H, q, J = 7.1 Hz), 3.03 (1 H, m), 3.16 (1 H, m), 3.55 (3 H, s), 4.32-4.44 (2 H, m), 4.98 (2 H, s), 5.04 (2 H, s), 6.56 (1 H, d, J = 8.5 Hz), 7.40 (1 H, d, J = 8.5 Hz), 7.68-7.76 (3 H, m), 8.11 (2 H, s). |

TABLE 1-continued

| Example | Chemical formula | Physicochemical properties |
| --- | --- | --- |
| 13 | | ¹H-NMR (CDCl₃) δ: 0.93 (3 H, t, J = 7.1 Hz), 1.04-1.18 (2 H, m), 1.35-1.65 (6 H, m), 1.86 (1 H, m), 2.75 (2 H, d, J = 7.6 Hz), 2.86 (2 H, q, J = 7.1 Hz), 3.07 (3 H, s), 3.42 (2 H, t, J = 5.4 Hz), 3.56 (3 H, s), 4.39 (2 H, t, J = 5.4 Hz), 4.99 (2 H, s), 5.04 (2 H, s), 6.57 (1 H, d, J = 8.7 Hz), 7.41 (1 H, d, J = 8.7 Hz), 7.71-7.77 (3 H, m), 8.10 (2 H, s). |
| 14 | | ¹H-NMR (CDCl₃) δ: 0.93 (3 H, t, J = 7.1 Hz), 1.02-1.18 (2 H, m), 1.35-1.66 (6 H, m), 1.86 (1 H, m), 2.20 (3 H, s), 2.76 (2 H, d, J = 7.5 Hz), 2.78-2.92 (4 H, m), 3.57 (3 H, s), 4.11 (2 H, t, J = 6.7 Hz), 4.90 (2 H, s), 5.01 (2 H, s), 6.56 (1 H, d, J = 8.6 Hz), 7.30-7.70 (5 H, m), 8.08 (2 H, s). |
| 15 | | ¹H-NMR (CDCl₃) δ: 0.93 (3 H, t, J = 7.1 Hz), 1.04-1.18 (2 H, m), 1.37-1.70 (6 H, m), 1.86 (1 H, m), 2.70 (3 H, s), 2.76 (2 H, d, J = 7.6 Hz), 2.86 (2 H, q, J = 7.1 Hz), 3.01 (1 H, m), 3.16 (1 H, m), 3.58 (3 H, s), 4.30-4.44 (2 H, m), 4.91 (2 H, s), 5.01 (2 H, s), 6.56 (1 H, d, J = 8.5 Hz), 7.30-7.64 (5 H, m), 8.10 (2 H, s). |
| 16 | | ¹H-NMR (CDCl₃) δ: 0.91 (3 H, t, J = 7.1 Hz), 1.02-1.18 (2 H, m), 1.35-1.70 (6 H, m), 1.84 (1 H, m), 2.19 (3 H, s), 2.74 (2 H, d, J = 7.5 Hz), 2.78-2.92 (4 H, m), 3.60 (3 H, s), 4.11 (2 H, t, J = 6.9 Hz), 5.02 (2 H, s), 5.21 (2 H, s), 6.57 (1 H, d, J = 8.7 Hz), 7.40 (1 H, d, J = 8.7 Hz), 7.58 (1 H, m), 7.73-7.79 (2 H, m), 8.07 (2 H, s). |

TABLE 1-continued

| Example | Chemical formula | Physicochemical properties |
|---|---|---|
| 17 | | ¹H-NMR (CDCl₃) δ: 0.92 (3 H, t, J = 7.1 Hz), 1.02-1.16 (2 H, m), 1.33-1.70 (6 H, m), 1.84 (1 H, m), 2.69 (3 H, s), 2.75 (2 H, d, J = 7.4 Hz), 2.86 (2 H, q, J = 7.1 Hz), 3.02 (1 H, m), 3.15 (1 H, m), 3.61 (3 H, s), 4.31-4.44 (2 H, m), 5.02 (2 H, s), 5.22 (2 H, s), 6.58 (1 H, d, J = 8.7 Hz), 7.41 (1 H, d, J = 8.7 Hz), 7.59 (1 H, d, J = 8.3 Hz), 7.73-7.79 (2 H, m), 8.08 (2 H, s). |
| 18 | | ¹H-NMR (CDCl₃) δ: 0.93 (3 H, t, J = 7.1 Hz), 1.05-1.19 (2 H, m), 1.35-1.65 (6 H, m), 1.86 (1 H, m), 2.19 (3 H, s), 2.76 (2 H, d, J = 7.5 Hz), 2.78-2.91 (4 H, m), 3.57 (3 H, s), 4.10 (2 H, t, J = 6.8 Hz), 4.86 (2 H, s), 5.00 (2 H, s), 6.56 (1 H, d, J = 8.6 Hz), 6.65 (1 H, t, J =9.0 Hz), 6.82 (2 H, d, J = 9.0 Hz), 7.40 (1 H, d, J = 8.6 Hz), 8.08 (2 H, s). |
| 19 | | ¹H-NMR (CDCl₃) δ: 0.94 (3 H, t, J = 7.1 Hz), 1.02-1.18 (2 H, m), 1.35-1.65 (6 H, m), 1.86 (1 H, m), 2.70 (3 H, s), 2.76 (2 H, d, J = 7.5 Hz), 2.86 (2 H, q, 7.1 Hz), 3.01 (1 H, m), 3.15 (1 H, m), 3.58 (3 H, s), 4.26-4.40 (2 H, m), 4.87 (2 H, s), 5.00 (2 H, s), 6.56 (1 H, d, J = 8.7 Hz), 6.65 (1 H, t, J =9.0 Hz), 6.81 (2 H, d, J = 9.0 Hz), 7.41 (1 H, d, J = 8.7 Hz), 8.10 (2 H, s). |
| 20 | | ¹H-NMR (CDCl₃) δ: 0.94 (3 H, t, J = 7.1 Hz), 1.05-1.22 (2 H, m), 1.35-1.70 (6 H, m), 1.86 (1 H, m), 2.76 (2 H, d, J = 7.5 Hz), 2.87 (2 H, q, J = 7.1 Hz), 3.06 (3 H, s), 3.42 (2 H, t, J = 5.4 Hz), 3.59 (3 H, s), 4.38 (2 H, t, J = 5.4 Hz), 4.88 (2 H, s), 5.00 (2 H, s), 6.57 (1 H, d, J = 8.8 Hz), 6.66 (1 H, t, J = 9.0 Hz), 6.81 (2 H, d, J = 9.0 Hz), 7.41 (1 H, d, J = 8.8 Hz), 8.09 (2 H, s). |

TABLE 1-continued

| Example | Chemical formula | Physicochemical properties |
|---|---|---|
| 21 | | ¹H-NMR (CDCl₃) δ: 0.95 (3 H, t, J = 7.1 Hz), 1.11-1.14 (2 H, m), 1.43-1.61 (6 H, m), 1.85 (1 H, m), 2.19 (3 H, s), 2.75 (2 H, d, J = 7.6 Hz), 2.81-2.89 (4 H, m), 3.71 (3 H, s), 4.10 (2 H, t, J = 6.6 Hz), 4.83 (2 H, s), 4.99 (2 H, s), 6.55 (1 H, d, J = 8.8 Hz), 7.20 (2 H, s), 7.22 (1 H, s), 7.39 (1 H, d, J = 8.8 Hz), 8.08 (2 H, s). |
| 22 | | IR (ATR)cm⁻¹: 2949, 1591, 1569, 1547, 1035.<br>¹H-NMR (CDCl₃) δ: 0.93 (3 H, t, J = 7.1 Hz), 1.10-1.16 (2 H, m), 1.43-1.62 (6 H, m), 1.86 (1 H, m), 2.69 (3 H, s), 2.75 (2 H, d, J = 7.6 Hz), 2.86 (2 H, q, J = 7.1 Hz), 3.03 (1 H, m), 3.16 (1 H, m), 3.57 (3 H, s), 4.29-4.33 (2 H, m), 4.84 (2 H, s), 4.99 (2 H, s), 6.55 (1 H, d, J = 8.8 Hz), 7.16 (2 H, s), 7.20 (1 H, s), 7.40 (1 H, d, J = 8.8 Hz), 8.10 (2 H, s). |
| 23 | | ¹H-NMR (CDCl₃) δ: 0.91 (3 H, t, J = 7.1 Hz), 1.10-1.13 (2 H, m), 1.36-1.61 (6 H, m), 1.87 (1 H, m), 2.19 (3 H, s), 2.74 (2 H, d, J = 7.6 Hz), 2.81-2.87 (4 H, m), 3.58 (3 H, s), 3.74 (6 H, s), 4.09 (2 H, t, J = 6.7 Hz), 4.85 (2 H, s), 4.98 (2 H, s), 6.39 (1 H, s), 6.44 (2 H, s), 6.54 (1 H, d, J = 8.8 Hz), 7.39 (1 H, d, J = 8.8 Hz), 8.08 (2 H, s). |
| 24 | | IR (ATR)cm⁻¹: 2945, 1596, 1545, 1058, 1035.<br>¹H-NMR (CDCl₃) δ: 0.92 (3 H, t, J = 7.1 Hz), 1.06-1.17 (2 H, m), 1.36-1.66 (6 H, m), 1.85 (1 H, m), 2.69 (3 H, s), 2.74 (2 H, d, J = 7.6 Hz), 2.84 (2 H, q, J = 7.1 Hz), 3.02 (1 H, m), 3.15 (1 H, m), 3.59 (3 H, s), 3.74 (6 H, s), 4.34-4.38 (2 H, m), 4.86 (2 H, s), 4.98 (2 H, s), 6.33 (1 H, t, J = 2.3 Hz), 6.44 (2 H, d, J = 2.3 Hz), 6.55 (1 H, d, J = 8.8 Hz), 7.39 (1 H, d, J = 8.8 Hz), 8.08 (2 H, s). |

TABLE 1-continued

| Example | Chemical formula | Physicochemical properties |
|---------|------------------|----------------------------|
| 25 | | IR (ATR)cm$^{-1}$: 2949, 1596, 1546, 1473, 1155, 1133.<br>$^1$H-NMR (CDCl$_3$) δ: 0.92 (3 H, t, J = 7.1 Hz), 1.09-1.14 (2 H, m), 1.42-1.60 (6 H, m), 1.84 (1 H, m), 2.74 (2 H, d, J = 7.3 Hz), 2.85 (2 H, q, J = 7.1 Hz), 3.06 (3 H, s), 3.40 (2 H, t, J = 5.4 Hz), 3.60 (3 H, s), 3.74 (6 H, s), 4.34 (2 H, t, J = 5.4 Hz), 4.87 (2 H, s), 4.98 (2 H, s), 6.32 (1 H, s), 6.44 (2 H, s), 6.55 (1 H, d, J = 8.5 Hz), 7.40 (1 H, d, J = 8.5 Hz), 8.07 (2 H, s). |
| 26 | | $^1$H-NMR (CDCl$_3$) δ: 0.92 (3 H, t, J = 7.1 Hz), 1.02-1.20 (2 H, m), 1.30-1.70 (6 H, m), 1.85 (1 H, m), 2.19 (3 H, s), 2.74 (2 H, d, J = 7.6 Hz), 2.78-2.92 (4 H, m), 3.58 (3 H, s), 4.10 (2 H, t, J = 6.7 Hz), 4.91 (2 H, s), 5.01 (2 H, s), 6.55 (1 H, d, J = 8.5 Hz), 7.07 (1 H, d, J = 7.8 Hz), 7.15 (1 H, s), 7.21 (1 H, d, J = 7.8 Hz), 7.30 (1 H, t, J = 7.8 Hz), 7.40 (1 H, d, J = 8.5 Hz), 8.09 (2 H, s) |
| 27 | | $^1$H-NMR (CDCl$_3$) δ: 0.92 (3 H, t, J = 7.1 Hz), 1.02-1.18 (2 H, m), 1.35-1.65 (6 H, m), 1.85 (1 H, m), 2.69 (3 H, s), 2.74 (2 H, d, J = 7.5 Hz), 2.85 (2 H, q, J = 7.1 Hz), 3.02 (1 H, m), 3.16 (1 H, m), 3.59 (3 H, s), 4.28-4.45 (2 H, m), 4.92 (2 H, s), 5.00 (2 H, s), 6.56 (1 H, d, J = 8.7 Hz), 7.00-7.35 (4 H, m), 7.40 (1 H, d, J = 8.7 Hz), 8.10 (2 H, s). |
| 28 | | $^1$H-NMR (CDCl$_3$) δ: 0.92 (3 H, t, J = 7.1 Hz), 1.02-1.17 (2 H, m), 1.35-1.66 (6 H, m), 1.85 (1 H, m), 2.75 (2 H, d, J = 7.4 Hz), 2.85 (2 H, q, J = 7.1 Hz), 3.08 (3 H, s), 3.41 (2 H, t, J = 5.4 Hz), 3.59 (3 H, s), 4.38 (2 H, t, J = 5.4 Hz), 4.92 (2 H, s), 5.00 (2 H, s), 6.57 (1 H, d, J = 8.5 Hz), 7.08 (1 H, d, J = 8.9 Hz), 7.14 (1 H, s), 7.20 (1 H, d, J = 8.9 Hz), 7.31 (1 H, t, J = 8.9 Hz), 7.41 (1 H, d, J = 8.5 Hz), 8.09 (2 H, s). |

TABLE 1-continued

| Example | Chemical formula | Physicochemical properties |
|---|---|---|
| 29 | | IR (ATR)cm$^{-1}$: 2954, 1605, 1501, 1474, 1033.<br>$^1$H-NMR (CDCl$_3$) δ: 0.91 (3 H, t, J = 7.1 Hz), 1.10-1.13 (2 H, m), 1.37-1.66 (6 H, m), 1.85 (1 H, m), 2.19 (3 H, s), 2.26 (6 H, s), 2.73 (2 H, d, J = 7.3 Hz), 2.81-2.86 (4 H, m), 3.58 (3 H, s), 4.09 (2 H, t, J = 6.6 Hz), 4.83 (2 H, s), 4.96 (2 H, s), 6.54 (1 H, d, J = 8.6 Hz), 6.84 (1 H, s), 6.88 (2 H, s), 7.38 (1 H, d, J = 8.6 Hz), 8.08 (2 H, s). |
| 30 | | IR (ATR)cm$^{-1}$: 2949, 1606, 1505, 1474, 1035.<br>$^1$H-NMR (CDCl$_3$) δ: 0.91 (3 H, t, J = 7.1 Hz), 1.08-1.13 (2 H, m), 1.41-1.67 (6 H, m), 1.85 (1 H, m), 2.26 (6 H, s), 2.69 (3 H, s), 2.73 (2 H, d, J = 7.6 Hz), 2.84 (2 H, q, J = 7.1 Hz), 3.02 (1 H, m), 3.16 (1 H, m), 3.59 (3 H, s), 4.32-4.41 (2 H, m), 4.84 (2 H, s), 4.96 (2 H, s), 6.54 (1 H, d, J = 8.6 Hz), 6.85 (1 H, s), 6.87 (2 H, s), 7.38 (1 H, d, J = 8.6 Hz), 8.09 (2 H, s). |
| 31 | | IR (ATR)cm$^{-1}$: 2951, 1469.<br>$^1$H-NMR (CDCl$_3$) δ: 0.95 (3 H, t, J = 7.1 Hz), 1.10-1.23 (2 H, m), 1.40-1.75 (6 H, m), 1.92 (1 H, m), 2.18 (3 H, s), 2.75 (2 H, d, J = 7.3 Hz), 2.80-2.90 (4 H, m), 3.57 (3 H, s), 4.08 (2 H, t, J = 6.6 Hz), 4.96 (2 H, s), 5.03 (2 H, s), 6.52 (1 H, d, J = 8.6 Hz), 6.74-6.94 (2 H, m), 7.18 (1 H, m), 7.39 (1 H, d, J = 8.6 Hz), 8.06 (2 H, s). |
| 32 | | $^1$H-NMR (CDCl$_3$) δ: 0.95 (3 H, t, J = 7.1 Hz), 1.10-1.75 (8 H, m), 1.90 (1 H, m), 2.68 (3 H, s), 2.76 (2 H, d, J = 7.3 Hz), 2.87 (2 H, q, J = 7.1 Hz), 3.01 (1 H, m), 3.15 (1 H, m), 3.58 (3 H, s), 4.32-4.37 (2 H, m), 4.96 (2 H, s), 5.04 (2 H, s), 6.53 (1 H, d, J = 8.6 Hz), 6.77-6.88 (2 H, m), 7.18 (1 H, m), 7.39 (1 H, d, J = 8.6 Hz), 8.09 (2 H, s). |

TABLE 1-continued

| Example | Chemical formula | Physicochemical properties |
|---|---|---|
| 33 | | $^1$H-NMR (CDCl$_3$) δ: 0.94 (3 H, t, J = 7.1 Hz), 1.10-1.60 (8 H, m), 1.86 (1 H, m), 2.19 (3 H, s), 2.76 (2 H, d, J = 7.3 Hz), 2.83 (2 H, t, J = 6.7 Hz), 2.86 (2 H, q, J = 7.1 Hz), 3.57 (3 H, s), 4.10 (2 H, t, J = 6.7 Hz), 4.90 (2 H, s), 5.03 (2 H, s), 6.55 (1 H, d, J = 8.6 Hz), 6.75-7.25 (3 H, m), 7.40 (1 H, d, J = 8.6 Hz), 8.09 (2 H, s). |
| 34 | | IR (ATR)cm$^{-1}$: 2948, 1606, 1548, 1488, 1475, 1035.<br>$^1$H-NMR (CDCl$_3$) δ: 0.94 (3 H, t, J = 7.1 Hz), 1.09-1.88 (9 H, m), 2.69 (3 H, s), 2.76 (2 H, d, J = 7.3 Hz), 2.87 (2 H, q, J = 7.1 Hz), 3.03 (1 H, m), 3.16 (1 H, m), 3.58 (3 H, s), 4.35-4.39 (2 H, m), 4.90 (2 H, s), 5.03 (2 H, s), 6.56 (1 H, d, J = 8.8 Hz), 6.86-7.15 (3 H, m), 7.40 (1 H, d, J = 8.8 Hz), 8.09 (2 H, s). |
| 35 | | $^1$H-NMR (CDCl$_3$) δ: 2948, 1617, 1474, 1426, 1285.<br>$^1$H-NMR (CDCl$_3$) δ: 0.92 (3 H, t, J = 7.1 Hz), 1.12-1.14 (2 H, m), 1.43-1.59 (6 H, m), 1.85 (1 H, m), 2.19 (3 H, s), 2.75 (2 H, d, J = 7.6 Hz), 2.82-2.88 (4 H, m), 3.57 (3 H, s), 4.10 (2 H, t, J = 6.7 Hz), 4.83 (2 H, s), 4.98 (2 H, s), 6.55 (1 H, d, J = 8.6 Hz), 6.98-7.20 (3 H, m), 7.39 (1 H, d, J = 8.6 Hz), 8.08 (2 H, s). |
| 36 | | $^1$H-NMR (CDCl$_3$) δ: 0.92 (3 H, t, J = 6.8 Hz), 1.05-1.17 (2 H, m), 1.37-1.67 (6 H, m), 1.86 (1 H, m), 2.69 (3 H, s), 2.72-2.76 (2 H, m), 2.83-2.87 (2 H, m), 3.03 (1 H, m), 3.14 (1 H, m), 3.58 (3 H, s), 4.35-4.39 (2 H, m), 4.84 (2 H, s), 4.97 (2 H, s), 6.56 (1 H, d, J = 8.6 Hz), 6.99-7.11 (3 H, m), 7.40 (1 H, d, J = 8.6 Hz), 8.09 (2 H, s). |

TABLE 1-continued

| Example | Chemical formula | Physicochemical properties |
|---|---|---|
| 37 | | ¹H-NMR (CDCl₃) δ: 0.93 (3 H, t, J = 7.1 Hz), 1.07-1.18 (2 H, m), 1.36-1.58 (6 H, m), 1.86 (1 H, m), 2.18 (3 H, s), 2.76 (2 H, d, J = 7.3 Hz), 2.83 (2 H, t, J = 6.6 Hz), 2.86 (2 H, q, J = 7.1 Hz), 3.58 (3 H, s), 4.09 (2 H, t, J = 6.6 Hz), 4.96 (2 H, s), 5.02 (2 H, s), 6.55 (1 H, d, J = 8.6 Hz), 6.98-7.15 (3 H, m), 7.40 (1 H, d, J = 8.6 Hz), 8.07 (2 H, s). |
| 38 | | IR (ATR)cm⁻¹: 2951, 1477. ¹H-NMR (CDCl₃) δ: 0.93 (3 H, t, J = 7.1 Hz), 1.06-1.18 (2 H, m), 1.33-1.66 (6 H, m), 1.87 (1 H, m), 2.75 (2 H, d, J = 7.6 Hz), 2.85 (2 H, q, J = 7.1 Hz), 3.55 (3 H, s), 4.94 (2 H, s), 5.02 (2 H, s), 5.06 (2 H, s), 6.55 (1 H, d, J = 8.6 Hz), 6.97-7.25 (6 H, m), 7.40 (1 H, d, J = 8.6 Hz), 8.10 (2 H, s). |
| 39 | | IR (ATR)cm⁻¹: 2948, 1477. ¹H-NMR (CDCl₃) δ: 0.94 (3 H, t, J = 7.3 Hz), 1.09-1.93 (9 H, m), 2.69 (3 H, s), 2.76 (2 H, d, J = 7.3 Hz), 2.86 (2 H, q, J = 7.3 Hz), 2.97-3.21 (2 H, m), 3.58 (3 H, s), 4.34-4.37 (2 H, m), 4.96 (2 H, s), 5.02 (2 H, s), 6.56 (1 H, d, J = 8.6 Hz), 6.99-7.42 (3 H, m), 7.40 (1 H, d, J = 8.6 Hz), 8.08 (2 H, s). |
| 40 | | ¹H-NMR (CDCl₃) δ: 0.96 (3 H, t, J = 7.1 Hz), 1.08-1.23 (2 H, m), 1.35-1.70 (6 H, m), 1.88 (1 H, m), 2.20 (3 H, s), 2.78 (2 H, d, J = 7.3 Hz), 2.85 (2 H, t, J = 6.6 Hz), 2.89 (2 H, q, J = 7.1 Hz), 3.55 (3 H, s), 4.12 (2 H, t, J = 6.6 Hz), 4.90 (2 H, s), 5.05 (2 H, s), 6.57 (1 H, d, J = 8.7 Hz), 7.42 (1 H, d, J = 8.7 Hz), 7.78 (1 H, s), 7.82 (2 H, s), 8.08 (2 H, s). |

TABLE 1-continued

| Example | Chemical formula | Physicochemical properties |
|---|---|---|
| 41 | | $^1$H-NMR (CDCl$_3$) δ: 0.96 (3 H, t, J = 7.1 Hz), 1.06-1.24 (2 H, m), 1.35-1.75 (6 H, m), 1.88 (1 H, m), 2.70 (3 H, s), 2.78 (2 H, d, J = 7.5 Hz), 2.88 (2 H, q, J = 7.1 Hz), 3.03 (1 H, m), 3.16 (1 H, m), 3.56 (3 H, s), 4.26-4.48 (2 H, m), 4.91 (2 H, s), 5.05 (2 H, s), 6.57 (1 H, d, J = 8.8 Hz), 7.42 (1 H, d, J = 8.8 Hz), 7.78 (1 H, s), 7.81 (2 H, s), 8.10 (2 H, s). |
| 42 | | $^1$H-NMR (CDCl$_3$) δ: 0.96 (3 H, t, J = 7.1 Hz), 1.08-1.24 (2 H, m), 1.40-1.75 (6 H, m), 1.89 (1 H, m), 2.79 (2 H, d, J = 7.4 Hz), 2.89 (2 H, q, J = 7.1 Hz), 3.07 (3 H, s), 3.43 (2 H, t, J = 5.4 Hz), 3.57 (3 H, s), 4.40 (2 H, t, J = 5.4 Hz), 4.92 (2 H, s), 5.05 (2 H, s), 6.58 (1 H, d, J = 8.6 Hz), 7.43 (1 H, d, J = 8.6 Hz), 7.79 (1 H, s), 7.81 (2 H, s), 8.09 (2 H, s). |
| 43 | | IR (ATR)cm$^{-1}$: 2951, 1500, 1475, 1067.<br>$^1$H-NMR (CDCl$_3$) δ: 0.91 (3 H, t, J = 7.1 Hz), 1.08-1.25 (2 H, m), 1.44-1.60 (6 H, m), 1.84 (1 H, m), 2.20 (3 H, s), 2.74 (2 H, d, J = 7.6 Hz), 2.81-2.85 (4 H, m), 3.58 (3 H, s), 4.10 (2 H, t, J = 6.8 Hz), 4.94 (2 H, s), 5.00 (2 H, s), 6.56 (1 H, d, J = 8.6 Hz), 7.37-7.41 (3 H, m), 7.53 (2 H, d, J = 8.6 Hz), 8.08 (2 H, s). |
| 44 | | IR (ATR)cm$^{-1}$: 2948, 1607, 1547, 1066.<br>$^1$H-NMR (CDCl$_3$) δ: 0.92 (3 H, t, J = 7.0 Hz), 1.06-1.13 (2 H, m), 1.41-1.61 (6 H, m), 1.85 (1 H, m), 2.69 (3 H, s), 2.74 (2 H, d, J = 7.6 Hz), 2.84 (2 H, q, J = 7.0 Hz), 3.01-3.21 (2 H, m), 3.59 (3 H, s), 4.33-4.43 (2 H, m), 4.95 (2 H, s), 5.00 (2 H, s), 6.56 (1 H, d, J = 8.6 Hz), 7.39 (2 H, d, J = 7.8 Hz), 7.40 (1 H, d, J = 8.6 Hz), 7.54 (2 H, d, J = 7.8 Hz), 8.09 (2 H, s). |

TABLE 1-continued

| Example | Chemical formula | Physicochemical properties |
| --- | --- | --- |
| 45 | | IR (ATR)cm$^{-1}$: 2949, 1607, 1548, 1500, 1475, 1033.<br>$^1$H-NMR (CDCl$_3$) δ: 0.92 (3 H, t, J = 7.1 Hz), 1.10-1.13 (2 H, m), 1.42-1.62 (6 H, m), 1.84 (1 H, m), 2.75 (2 H, d, J = 7.3 Hz), 2.85 (2 H, q, J = 7.1 Hz), 3.06 (3 H, s), 3.41 (2 H, t, J = 5.3 Hz), 3.60 (3 H, s), 4.37 (2 H, t, J = 5.3 Hz), 4.96 (2 H, s), 5.01 (2 H, s), 6.57 (1 H, d, J = 8.6 Hz), 7.39 (1 H, d, J = 8.6 Hz), 7.41 (2 H, d, J = 8.3 Hz), 7.55 (2 H, d, J = 8.3 Hz), 8.09 (2 H, s). |
| 46 | | $^1$H-NMR (CDCl$_3$) δ: 0.92 (3 H, t, J = 7.1 Hz), 1.03-1.20 (2 H, m), 1.35-1.70 (6 H, m), 1.85 (1 H, m), 2.75 (2 H, d, J = 7.8 Hz), 2.85 (2 H, q, J = 7.1 Hz), 3.57 (3 H, s), 4.99 (2 H, s), 5.03 (2 H, s), 6.58 (1 H, d, J = 8.8 Hz), 7.43 (1 H, d, J = 8.8 Hz), 7.72-7.75 (3 H, m), 8.30 (2 H, s). |
| 47 | | $^1$H-NMR (CDCl$_3$) δ: 0.92 (3 H, t, J = 6.8 Hz), 1.03-1.23 (2 H, m), 1.30-1.75 (6 H, m), 1.86 (1 H, m), 2.75 (2 H, d, J = 7.3 Hz), 2.86 (2 H, q, J = 6.8 Hz), 2.98-3.01 (4 H, m), 3.54 (3 H, s), 3.83-3.89 (4 H, m), 4.98 (2 H, s), 5.05 (2 H, s), 6.56 (1 H, d, J = 8.6 Hz), 7.40 (1 H, d, J = 8.6 Hz), 7.65-7.80 (3 H, m), 8.10 (2 H, s). |
| 48 | | $^1$H-NMR (CDCl$_3$) δ: 0.91 (3 H, t, J = 7.1 Hz), 1.08-1.13 (2 H, m), 1.39-1.74 (12 H, m), 1.85 (1 H, m), 2.74 (2 H, d, J = 7.6 Hz), 2.85 (2 H, q, J = 7.1 Hz), 2.96 (4 H, t, J = 5.1 Hz), 3.53 (3 H, s), 4.97 (2 H, s), 5.05 (2 H, s), 6.55 (1 H, d, J = 8.6 Hz), 7.39 (1 H, d, J = 8.6 Hz), 7.71 (1 H, s), 7.74 (2 H, s), 8.11 (2 H, s). |

TABLE 1-continued

| Example | Chemical formula | Physicochemical properties |
|---|---|---|
| 49 | | $^1$H-NMR (CDCl$_3$) δ: 1.84-1.91 (4 H, m), 2.20 (3 H, s), 2.85 (2 H, t, J = 6.8 Hz), 3.01 (4 H, t, J = 6.5 Hz), 3.51 (3 H, s), 4.12 (2 H, t, J = 6.5 Hz), 4.90 (2 H, s), 4.97 (2 H, s), 6.49 (1 H, d, J = 8.6 Hz), 7.25 (1 H, d, J = 8.6 Hz), 7.70 (3 H, s), 8.12 (2 H, s). |
| 50 | | IR (ATR)cm$^{-1}$: 1496, 1473, 1425, 1038.<br>$^1$H-NMR (CDCl$_3$) δ: 1.88-1.93 (4 H, m), 2.70 (3 H, s), 3.00-3.20 (6 H, m), 3.52 (3 H, s), 4.36-4.42 (2 H, m), 4.91 (2 H, s), 4.97 (2 H, s), 6.50 (1 H, d, J = 8.8 Hz), 7.26 (1 H, d, J = 8.8 Hz), 7.70 (3 H, s), 8.14 (2 H, s). |
| 51 | | IR (ATR)cm$^{-1}$: 1498, 1474, 1425, 1129.<br>$^1$H-NMR (CDCl$_3$) δ: 1.86-1.93 (4 H, m), 3.02 (4 H, t, J = 6.4 Hz), 3.07 (3 H, s), 3.43 (2 H, d, J = 5.4 Hz), 3.52 (3 H, s), 4.40 (2 H, t, J = 5.4 Hz), 4.92 (2 H, s), 4.97 (2 H, s), 6.51 (1 H, d, J = 8.5 Hz), 7.27 (1 H, d, J = 8.5 Hz), 7.70 (3 H, s), 8.13 (2 H, s). |
| 52 | | $^1$H-NMR (CDCl$_3$) δ: 0.93 (3 H, t, J = 7.2 Hz), 0.98-1.10 (2 H, m), 1.35-1.70 (6 H, m), 1.82 (1 H, m), 2.61 (2 H, d, J = 7.4 Hz), 2.76 (2 H, q, J = 7.2 Hz), 3.08 (3 H, s), 3.47 (2 H, t, J = 5.4 Hz), 4.46 (2 H, t, J = 5.4 Hz), 4.86 (2 H, s), 4.90 (2 H, s), 6.52 (1 H, J = 9.7 Hz), 7.43 (1 H, d, J = 9.7 Hz), 7.68 (2 H, s), 7.78 (1 H, s), 8.21 (2 H, s), 10.2 (1 H, br). |

TABLE 1-continued

| Example | Chemical formula | Physicochemical properties |
|---|---|---|
| 53 | | IR (ATR)cm$^{-1}$: 2953, 1498, 1475, 1035.<br>$^1$H-NMR (CDCl$_3$) δ: 0.92 (3 H, t, J = 7.3 Hz), 1.10-1.60 (8 H, m), 1.83 (1 H, m), 2.19 (3 H, s), 2.75 (2 H, d, J = 7.3 Hz), 2.82-2.86 (4 H, m), 3.57 (3 H, s), 4.10 (2 H, t, J = 6.6 Hz), 4.93 (2 H, s), 5.01 (2 H, s), 6.56 (1 H, d, J = 8.8 Hz), 7.39 (2 H, d, J = 8.3 Hz), 7.40 (1 H, d, J = 8.8 Hz), 7.58 (2 H, d, J = 8.3 Hz), 8.07 (2 H, s). |
| 54 | | $^1$H-NMR (CDCl$_3$) δ: 0.92 (3 H, t, J = 7.1 Hz), 1.08-1.13 (2 H, m), 1.41-1.67 (6 H, m), 1.83 (1 H, m), 2.69 (3 H, s), 2.75 (2 H, d, J = 7.4 Hz), 2.85 (2 H, q, J = 7.1 Hz), 2.99-3.19 (2 H, m), 3.58 (3 H, s), 4.33-4.42 (2 H, m), 4.94 (2 H, s), 5.01 (2 H, s), 6.57 (1 H, d, J = 8.8 Hz), 7.39 (2 H, d, J = 8.3 Hz), 7.41 (1 H, d, J = 8.8 Hz), 7.58 (2 H, d, J = 8.3 Hz), 8.09 (2 H, s). |
| 55 | | $^1$H-NMR (CDCl$_3$) δ: 0.92 (3 H, t, J = 7.1 Hz), 2.19 (3 H, s), 2.83 (2 H, t, J = 6.8 Hz), 2.88 (2 H, q, J = 7.1 Hz), 3.55 (3 H, s), 3.72 (3 H, s), 3.92 (2 H, s), 4.10 (2 H, t, J = 6.8 Hz), 4.85 (2 H, s), 5.03 (2 H, s), 6.56 (1 H, d, J = 8.5 Hz), 6.73 (2 H, d, J = 8.5 Hz), 7.10 (2 H, d, J = 8.5 Hz), 7.38 (1 H, d, J = 8.5 Hz), 7.71 (2 H, s), 7.72 (1 H, s), 8.07 (2 H, s). |

Test Example 1

CETP Inhibitory Action in Human Plasma

A solution obtained by dissolving an exemplary compound or a comparative compound in polyethyleneglycol/N-methyl-2-pyrrolidone (vol/vol=1/1) was added to human plasma, and the mixture was incubated in an incubator at 37° C. for 4 hours. The CETP activity in this plasma was measured with Cholesteryl Ester Transfer Protein Activity kit (Roar Biomedical, catalog No.: RB-CETP). Specifically, to each well of a 96-well plate, 95 μL of a buffer (10 mM Tris, 150 mM NaCl, 2 mM EDTA, pH 7.4), 2 μL of Donor particle and 2 μL of Acceptor particle were added, 1 μL of the human plasma after the incubation was added to the mixture, and the mixture was incubated in an incubator at 37° C. for 2 hours.

After completion of the incubation, fluorescence intensity (FLU) was measured with a fluorescence plate reader (excitation wavelength: 465 nm, emission wavelength: 535 nm). In accordance with the following equation 1, the CETP activity (% of control) was obtained for the compounds of the examples and the comparative compounds for two or more concentrations.

CETP activity (% of control)=(Sample FLU−Blank FLU)×100/(Control FLU−Blank FLU)  (Equation 1)

In the equation, the terms have the following meanings:

Blank: No addition of plasma

Control: Plasma not added with solution of compound

Sample: Plasma added with solution of compound

A value obtained by subtracting the value of the CETP activity from 100 was defined as the CETP inhibitory rate of each exemplary compound and comparative compound, and a concentration inhibiting the CETP activity by 50% ($IC_{50}$) was calculated for each exemplary compound and comparative compound from the values of the CETP inhibitory rate at two or more concentrations. The results are shown in Table 2. As the comparative compounds, the following compounds were used, which are compounds having a benzyl(heterocyclylmethyl)amine structure described in Examples 52, 66 and 79 of Patent document 9 (International Patent Publication WO2006/073973).

[Formula 5]

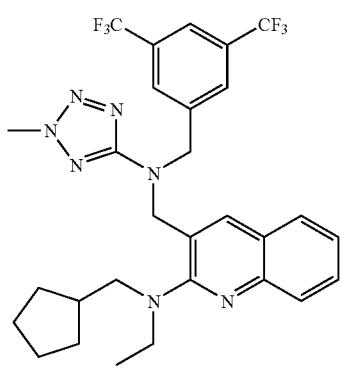

Comparative Compound 1

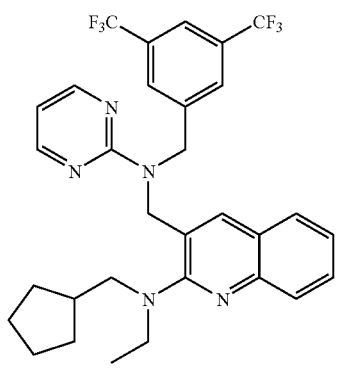

Comparative Compound 2

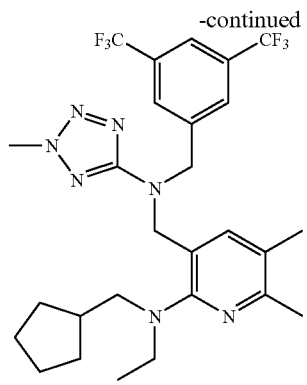

Comparative Compound 3

TABLE 2

| Compound | $IC_{50}$ (μM) |
| --- | --- |
| Example 9 | 0.09 |
| Example 10 | 0.035 |
| Example 12 | 0.35 |
| Example 13 | 0.25 |
| Example 41 | 0.5 |
| Example 42 | 0.25 |
| Comparative Compound 1 | 1.0 |
| Comparative Compound 2 | 20.0 |
| Comparative Compound 3 | 1.5 |

From the aforementioned test results, it was revealed that the pyrimidine compounds of the present invention having a benzyl(pyridylmethyl)amine structure, salts thereof and solvates thereof had superior CETP inhibitory activity compared with Comparative Compound 1 which is considered as one of the compounds having the most potent activity among the compounds described in Patent document 9, Comparative Compound 2 which does not have a pyridylmethyl structure, or Comparative Compound 3 which does not have a pyrimidine structure.

Test Example 2

Measurement of CETP Inhibitory Activity in Blood of Hamster (Single Oral Administration)

1: Labeling of Donor Lipoprotein ($HDL_3$ Fraction) with $^3$H-Cholesterol and Preparation of Acceptor Lipoprotein (LDL Fraction)

The donor lipoprotein was prepared by adding KBr to plasma of healthy human subject (50 mL) to adjust the specific gravity (d) of the plasma to be 1.125, centrifuging the mixture at 100,000 rpm and 4° C. for 2.5 hours (Optima Max-E TLA-100.2 rotor, Beckman), and collecting the lower layer ($HDL_3$ fraction, d>1.125). The resulting fraction was dialyzed against PBS (10 mM $Na_2HPO_4$, 10 mM $NaH_2PO_4$, 0.15 M NaCl, 1 mM EDTA-2Na, pH 7.4). Then, a 95% ethanol solution of 9.25 MBq 1, 2-3H(N)cholesterol (NEN™, Life Science Products, USA) was added to the sample with stirring, and the mixture was incubated at 37° C. for 18 hours. After the incubation, the mixture was added with KBr to adjust the specific gravity thereof to be 1.210, and centrifuged under the same conditions as mentioned above to obtain the upper layer ($^3$H-labeled $HDL_3$ fraction, 1.125<d<1.210). The $^3$H-labeled $HDL_3$ was dialyzed against PBS, and used for the measurement of the CETP activity.

The acceptor lipoprotein was prepared as follows. Plasma of healthy human subject (30 mL) was centrifuged under the same conditions as mentioned above, and the upper layer (chylomicron and VLDL fraction, d<1.006) was removed. The lower layer was added with KBr to adjust the specific gravity thereof to be 1.063, and centrifuged under the same conditions to obtain the upper layer (LDL fraction, 1.006<d<1.063). The LDL fraction was dialyzed against PBS and used for the measurement of the CETP activity.

2: Measurement of CETP Inhibitory Activity

Each of the compounds of Examples 10 and 13 and the comparative compounds was dissolved in olive oil and orally administered once to the animals, and blood was collected from the abdominal portion of vena cava under pentobarbital anesthetization 2 hours after the administration. Further, as a control, olive oil in which any compound was not dissolved was administered, and blood was collected in a similar manner (n=3 for each).

To 10 µL of the hamster plasma, 5 µL of $^3$H-labeled $HDL_3$ and 20 µL of LDL were added, and the final volume of the mixture was made 600 mL with a TBS solution (10 mM Tris, 0.15 M NaCl, pH 7.4). The mixture was incubated at 37° C. for 18 hours, then added with 400 µL of the TBS solution containing 0.15 M $MgCl_2$ and 0.3% dextran sulfate, stirred (10 sec×2) with VORTEX-2 (Scientific Industries Inc.), left for 30 minutes on ice, and centrifuged at 4° C. and 8,000 rpm for 10 minutes (MX-301, TOMY). The resulting centrifugation supernatant ($^3$H-labeled $HDL_3$ fraction) in a volume of 300 µL was collected in a vial, and added with 3.6 mL of a scintillator (Aquazol-2, Packard), and the mixture was stirred. Then, radioactivity of $^3$H was measured with a liquid scintillation counter (TRI-CARB 2700 TR, Packard). The CETP activity (%) was obtained in accordance with the following equation 2. The results are shown in Table 3.

CETP activity (%)=(Blank dpm−Sample dpm)×100/(Blank dpm)  (Equation 2)

In the equation, the terms have the following meanings:

Blank dpm: Value of $^3$H radioactivity of sample not added with plasma

Sample dpm: Value of $^3$H radioactivity of sample added with compound or control sample.

TABLE 3

| Compound | Dose (mg/kg) | Average CETP activity ± standard deviation (%) |
|---|---|---|
| Control | — | 33.7 ± 2.3 |
| Example 10 | 30 | 2.6 ± 1.1 |
| Example 13 | 30 | 8.5 ± 1.7 |
| Comparative Compound 1 | 30 | 22.9 ± 3.3 |
| Comparative Compound 2 | 30 | 30.3 ± 4.2 |
| Comparative Compound 3 | 30 | 15.0 ± 4.0 |

From the aforementioned test results, it was revealed that the pyrimidine compounds of the present invention having a benzyl(pyridylmethyl)amine structure, salts thereof and solvates thereof had superior CETP inhibitory activity also in living bodies compared with Comparative Compound 1 which is considered one of the compounds showing the most potent activity among the compounds described in Patent document 9, Comparative Compound 2 which does not have a pyridylmethyl structure, or Comparative Compound 3 which does not have a pyrimidine structure.

Test Example 3

Measurement of CETP Inhibitory Activity in Blood of Hamster (Repetitive Oral Administration for 7 Days)

Each of the compounds of Examples 10 and 13 was suspended in 10% aqueous ethanol and 0.5% aqueous methylcellulose, respectively, and repetitively orally administered for 7 days (administered once a day), and blood was collected from the abdominal portion of vena cava under pentobarbital anesthetization 2 hours after the final administration. Further, as a control, 10% aqueous ethanol in which any compound was not suspended was administered, and blood was collected in a similar manner (n=5 for each).

The CETP activity (%) was obtained in the same manner as that of Test Example 2 mentioned above. The results are shown in Table 4.

TABLE 4

| Compound | Single dose (mg/kg) | Average CETP activity ± standard deviation (%) |
|---|---|---|
| Control | — | 43.5 ± 6.4 |
| Example 10 | 100 | 11.4 ± 6.0 |
| Example 13 | 100 | 9.0 ± 1.7 |

From the aforementioned test results, it was revealed that the pyrimidine compounds of the present invention having a benzyl(pyridylmethyl)amine structure, salts thereof and solvates thereof had superior CETP inhibitory activity also in living bodies.

INDUSTRIAL APPLICABILITY

The compounds of the present invention, salts thereof, and solvates thereof exhibit potent inhibitory activity on CETP, and can suitably be used as active ingredients of medicaments for prophylactic and/or therapeutic treatment of diseases including hyperlipidemia, arteriosclerosis, atherosclerosis, peripheral vascular disease, hyper-LDL-emia, hypo-HDL-emia, hypercholesterolemia, hypertriglyceridemia, familial hypercholesterolemia, cardiovascular disturbance, angina pectoris, ischemia, cardiac ischemia, thrombosis, myocardial infarction, reperfusion disturbance, angioplasty restenosis, hypertension, diabetic vascular complication, obesity, endotoxemia and the like.

What is claimed is:

1. A compound represented by the following general formula (I):

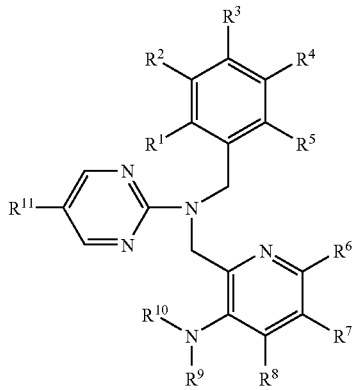

wherein,
R$^1$, R$^2$, R$^3$, R$^4$ and R$^5$ are the same or different, and represent hydrogen atom, a halogen atom, a lower alkyl group, a halo(lower alkyl) group, a lower alkoxy group, a halo(lower alkoxy) group, hydroxy group, cyano group, nitro group, a (lower alkyl)thio group, a (lower alkyl)sulfinyl group, a (lower alkyl)sulfonyl group, sulfonamido group, an amino group which may have a substituent, carboxyl group, a (lower alkyl)carbonyl group, or a (lower alkoxy)carbonyl group, R$^6$, R$^7$ and R$^8$ are the same or different, and represent hydrogen atom, a halogen atom, a lower alkyl group, a lower cycloalkyl group, a (lower cycloalkyl)(lower alkyl) group, a halo(lower alkyl) group, a lower alkoxy group, a halo(lower alkoxy) group, hydroxy group, cyano group, nitro group, a (lower alkyl)thio group, a (lower alkyl)sulfinyl group, a (lower alkyl)sulfonyl group, sulfonamido group, an amino group which may have a substituent, carboxyl group, a (lower alkyl)carbonyl group, or a (lower alkoxy)carbonyl group, R$^9$ and R$^{10}$ are the same or different, and represent hydrogen atom, a lower alkyl group, a (lower cycloalkyl)(lower alkyl) group, an aryl group, an aryl(lower alkyl) group which may have a substituent, or a lower cycloalkyl group, or may combine to form a nitrogen-containing saturated heterocyclic ring together with the adjacent nitrogen atom, and R$^{11}$ represents hydrogen atom, a halogen atom, a lower alkoxy group, a (lower alkyl)thio(lower alkoxy) group, a (lower alkyl)sulfinyl(lower alkoxy) group, a (lower alkyl)sulfonyl(lower alkoxy) group, an aryl(lower alkoxy) group which may have a substituent, a (lower alkyl)amino group, a di(lower alkyl)amino group, a (lower alkyl)thio(lower alkyl)amino group, a (lower alkyl)sulfinyl(lower alkyl)amino group, a (lower alkyl)sulfonyl(lower alkyl)amino group, an arylamino group, a cyclic amino group which may have a hetero atom as a ring-constituting atom, a (lower alkoxy)(lower alkoxy) group, a (lower alkoxy)(lower alkyl)amino group, a hydroxy(lower alkoxy) group, a hydroxy(lower alkyl) amino group, an acylamino group, a (lower alkyl)sulfonylamino group, a hydroxycarbonyl(lower alkoxy) group, an amino(lower alkoxy) group, a (lower alkyl) amino(lower alkoxy) group, or a di(lower alkyl)amino (lower alkoxy) group,
or a salt thereof.

2. The compound or a salt thereof according to claim 1, wherein R$^1$, R$^2$, R$^3$, R$^4$ and R$^5$ are the same or different, and represent hydrogen atom, a halogen atom, a C$_1$-C$_6$ alkyl group, a halo(C$_1$-C$_6$ alkyl) group, a C$_1$-C$_6$ alkoxy group, a halo(C$_1$-C$_6$ alkoxy) group, or cyano group, R$^6$, R$^7$ and R$^8$ are the same or different, and represent hydrogen atom, a C$_1$-C$_6$ alkoxy group, or hydroxy group, R$^9$ and R$^{10}$ are the same or different, and represent a C$_1$-C$_6$ alkyl group, a (C$_3$-C$_8$ cycloalkyl)(C$_1$-C$_6$ alkyl) group, or a (C$_6$-C$_{10}$ aryl)(C$_1$-C$_6$ alkyl) group which may have a C$_1$-C$_6$ alkoxy group on the aryl group as a substituent, or combine to form pyrrolidinyl group together with the adjacent nitrogen atom, and R$^{11}$ is a halogen atom, a (C$_1$-C$_6$ alkyl)thio(C$_1$-C$_6$ alkoxy) group, a (C$_1$-C$_6$ alkyl)sulfinyl(C$_1$-C$_6$ alkoxy) group, a (C$_1$-C$_6$ alkyl)sulfonyl(C$_1$-C$_6$ alkoxy) group, a (C$_6$-C$_{10}$ aryl)(C$_1$-C$_6$ alkoxy) group which may have 1 or 2 substituents selected from a halogen atom, a halo(C$_1$-C$_6$ alkyl) group and cyano group on the aryl group as a substituent, morpholinyl group, or piperidinyl group.

3. The compound or a salt thereof according to claim 1 or 2, wherein R$^1$, R$^2$, R$^3$, R$^4$ and R$^5$ are the same or different, and represent hydrogen atom, a halo(C$_1$-C$_6$ alkyl) group, or cyano group, R$^6$, R$^7$, and R$^8$ are the same or different, and represent hydrogen atom, or a C$_1$-C$_6$ alkoxy group, R$^9$ and R$^{10}$ are the same or different, and represent a (C$_3$-C$_8$ cycloalkyl)(C$_1$-C$_6$ alkyl) group, or a C$_1$-C$_6$ alkyl group, and R$^{11}$ is a (C$_1$-C$_6$ alkyl)thio(C$_1$-C$_6$ alkoxy) group, a (C$_1$-C$_6$ alkyl)sulfinyl(C$_1$-C$_6$ alkoxy) group, or a (C$_1$-C$_6$ alkyl) sulfonyl(C$_1$-C$_6$ alkoxy) group.

4. The compound or a salt thereof according to claim 1, wherein R$^1$, R$^2$, R$^3$, R$^4$, and R$^5$ are the same or different, and represent hydrogen atom, trifluoromethyl group, or cyano group, R$^6$, R$^7$ and R$^8$ are the same or different, and represent hydrogen atom, or methoxy group, R$^9$ and R$^{10}$ are the same or different, and represent cyclopentylmethyl group, or ethyl group, and R$^{11}$ is 2-methylthioethoxy group, 2-methylsulfinylethoxy group, or 2-methylsulfonylethoxy group.

5. A medicament composition containing the compound or a salt thereof according to claim 1 as an active ingredient.

6. A pharmaceutical composition containing the compound or a salt thereof according to claim 1 and a pharmaceutically acceptable carrier.

* * * * *